US009029629B2

(12) United States Patent
Hu et al.

(10) Patent No.: US 9,029,629 B2
(45) Date of Patent: May 12, 2015

(54) **ALTERED *FAD2* AND *FAD3* GENES IN *BRASSICA* AND THE MOLECULAR MARKER-ASSISTED DETECTION THEREOF**

(75) Inventors: Xueyi Hu, Westfield, IN (US); Mandy Lynne Sullivan-Gilbert, Carmel, IN (US); Manju Gupta, Carmel, IN (US); Steven Arnold Thompson, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 2636 days.

(21) Appl. No.: 10/545,100

(22) PCT Filed: Feb. 11, 2004

(86) PCT No.: PCT/US2004/003852
§ 371 (c)(1),
(2), (4) Date: May 16, 2006

(87) PCT Pub. No.: WO2004/072259
PCT Pub. Date: Aug. 26, 2004

(65) Prior Publication Data
US 2006/0248611 A1    Nov. 2, 2006

Related U.S. Application Data

(60) Provisional application No. 60/446,429, filed on Feb. 11, 2003.

(51) Int. Cl.
| | | |
|---|---|---|
| *A01H 1/02* | (2006.01) | |
| *A01H 1/04* | (2006.01) | |
| *A01H 5/00* | (2006.01) | |
| *C12N 9/02* | (2006.01) | |
| *C12N 15/82* | (2006.01) | |

(52) U.S. Cl.
CPC .............. *A01H 1/04* (2013.01); *C12N 9/0083* (2013.01); *C12N 15/8247* (2013.01)

(58) Field of Classification Search
USPC .................................................. 800/267, 306
See application file for complete search history.

(56) References Cited

U.S. PATENT DOCUMENTS

| | | | |
|---|---|---|---|
| 5,638,637 A | 6/1997 | Wong et al. | |
| 5,840,946 A | 11/1998 | Wong et al. | |
| 5,850,026 A | 12/1998 | DeBonte et al. | |
| 5,965,755 A | 10/1999 | Sernyk et al. | |
| 6,169,190 B1 | 1/2001 | Lanuza et al. | |
| 6,441,278 B1 | 8/2002 | DeBonte et al. | |

FOREIGN PATENT DOCUMENTS

| | | | |
|---|---|---|---|
| WO | WO 01/25453 | * | 4/2001 |
| WO | 2004072259 A2 | | 8/2004 |

OTHER PUBLICATIONS

Rajcan et al. 1999. Euphytica 105: 173-181.*
Jourdren et al. Theor Appl Genet 93: 512-518, 1996a.*
Jourdren et al. Euphytica 90: 351-357, 1996b.*
Somers et al. Theor Appl Genet 96: 897-903, 1998.*
Maniatis et al. Molecular Cloning: A Laboratory Manual, Cold Spring Harbor Laboratory, 1982; see in particular pp. 387-389.*
Arondel, V., et al., Map based cloning of a gene controlling Omega 3 fatty acid desaturation in *Arabidopsis*, Science, 1992, pp. 1353-1355, vol. 258.
Auld, D.K., et al., Rapeseed mutants with reduced levels of polyunsaturated fatty acids and increased levels of oleic acid, Crop Sci., 1992, pp. 657-662, vol. 32.
Brown, J.W.S., *Arabidopsis* intron mutations and pre mRNA splicing, Plant J., 1996, pp. 771-780, vol. 10.
Brunel, D., et al., Development of amplified consensus genetic markers (ACGM) in *Brassica napus* from *Arabidopsis thaliana* sequences of known biological function, Genome, 1999, pp. 387-402, vol. 12.
Canvin, D.T., The effect of temperature on the oil content and fatty acid composition of the oils from several oil seed crops, Canadian Journal of Botany, 1965, pp. 63-69, vol. 43.
Chen, J.L., et al., A comparison of traditional and haploid derived populations of oilseed rape (*Brassica napus* L.) for fatty acid composition of the seed oil, Euphytica, 1990, pp. 59-65, vol. 51.
Deng, X., et al., Temperature effects on fatty acid composition during development of low linolenic oilseed rape (*Brassica napus* L.), Journal of the American Oil Chemists' Society,1998, pp. 759-766, vol. 75.
Hu, J., et al., (1995). Mapping of a gene determining linolenic acid concentration in rapeseed with DNA based markers, Theor. Appl. Genet., 1995, pp. 258-262, vol. 90.
Hu, J., et al., SCAR and RAPD markers associated with 18 carbon fatty acids in rapeseed, *Brassica napus*, Plant Breeding, 1999, pp. 145-150.vol. 118.
Kondra, Z.P., et al., Inheritance of oleic, linoleic and linolenic acids in seed oil of rapeseed (*Brassica napus*), Can. J. Plant Sci., 1975, pp. 205-210, vol. 55.

(Continued)

*Primary Examiner* — Eileen B O Hara
(74) *Attorney, Agent, or Firm* — Marcia I. Rosenfeld; TraskBritt, P.C.

(57) ABSTRACT

The present invention provides methods of marker-assisted selection for high oleic/low linolenic traits in canola and in other oil seed crop species, as well as isolated nucleic acids for use as molecular markers in such methods. In particular, molecular markers and *Brassica* nucleic acid corresponding to fad2 and fad3 gene mutations are disclosed. The markers of the present invention are highly useful for the direct selection of desirable fad2 and fad3 alleles during marker-assisted trait introgression and breeding. In one aspect of the embodiment, two single nucleotide polymorphism (SNP) markers are provided that correspond to the alleles. Thus, the present invention advantageously permits one of skill in the art to breed for the molecular markers described herein, or derivatives thereof, rather than breeding for a high oleic/low linolenic phenotype.

15 Claims, 12 Drawing Sheets

(56) References Cited

OTHER PUBLICATIONS

Lorkovic, Z.J., Pre mRNA splicing in higher plants, Trends in Plant Science, 2000, pp. 160-167, vol. 5.
McCullough, A.J., et al., Factors Affecting Authentic 5' Splice Site Selection in Plant Nuclei, Mol. Cell. Biol., 1993, pp. 1323-1331, vol. 13.
Nishiuchi, T., et al., Genomic nucleotide sequence of a gene encoding a microsomal w-3 fatty acid desaturase from *Arabidopsis thaliana*, Plant Physiol., 1994, pp. 767-768, vol. 105.
Rucker, B., et al., Impact of low linolenic acid content on seed yield of winter oilseed rape (*Brassica napus* L.), Plant Breeding, 1996, pp. 226-230, vol. 115.
Scheffler, J.A., et al., Desaturase Multigene Families of *Brassica napus* Arose Through Genome Duplication, Theor. Appl. Genet., 1997, pp. 583-591, vol. 94, Springer-Verlag 1997.
Schierholt, A., et al., Inheritance of High Oleic Acid Mutations in Winter Oilseed Rape (*Brassica napus* L.), Crop Sci., 2001, pp. 1444-1449, vol. 41.
Schierholt, A., et al., Mapping a High Oleic Acid Mutation in Winter Oilseed Rape (*Brassica napus* L.), Theor. Appl. Genet., 2000, pp. 897-901, vol. 101.
Simpson, Craig G., et al., Characterization of Exon Skipping Mutants of the COP1 Gene from *Arabidopsis*, The Plant Journal, 1998, pp. 125-131 vol. 15(1), Blackwell Science Ltd.
Song, K.M., et al., A Linkage Map of *Brassica rapa* (syn. campestris) Based on Restriction Fragment Length Polymorphism Loci, Theor. Appl. Genet., pp. 296-304, vol. 82, 1991.
Tanhuanpää, P., et al., Mapping of Genes Affecting Linolenic Acid Content in *Brassica rapa, Brassica rapa* subsp. Oleifera Omega-3 Fatty Acid Desaturase (Fad3) gene, partial cds, GenBank direct submission, GenBank Accession AF308975, AF308976, AF308977 and AF308978, Oct. 4, 2002, 4 pages.
Tanhuanpää, P., et al., Mapping and Cloning of FAD2 Gene to Develop Allele-Specific PCR for Oleic Acid in Spring Turnip Rape (*Brassica rapa* ssp. oleifera), Molecular Breeding, 1998, pp. 543-550, vol. 4.
Tanhuanpää P., et al., Mapping of Genes Affecting Linolenic Acid Content in *Brasssica rapa* Ssp. Oleifera, Molecular Breeding, 2002, pp. 51-62, vol. 10, No. 1-2.
Tanhuanpää P.K., et al., Association of a RAPD Marker With Linolenic Acid Concentration in the Seed Oil of Rapeseed (*Brassica napus* L.), Genome, 1995, pp. 414-416, vol. 38.
Thormann, C.E., et al. Mapping Loci Controlling the Concentrations of Erucic and Linolenic Acids in Seed Oil of *Brassica napus* L., Theor. App. Genet., 1996, pp. 282-286, vol. 93.
Yadav, Narendra S., et al., Cloning of Higher Plant w-3 Fatty Acid Desaturases, Plant Physiol., 1993, pp. 467-476, vol. 103.
Yermanos, D.M., et al., Effects of Temperatures During Plant Development on Fatty Acid Composition of Linseed Oil, Agronomy J., 1965, pp. 453-454, vol. 57.
Carrillo, Humberto, et al., The Multiple Sequence Alignment Problem in Biology, SIAM J. Appl. Math., 1988, pp. 1073-1082, Vo.. 48, No. 5, Society for Industrial and Applied Mathematics.
Devereux, John, et al., A Comprehensive Set of Sequence Analysis, Programs for the VAX, Nucleic Acids Research, 1984, pp. 387-395, vol. 12, No. 1.
Altschul, Stephen F., et al., Basic Local Alignment Search Tool, J. Mol. Biol., 1990, pp. 403-410, vol. 215.
Supplementary European Search Report for Application No. EP 04 71 0183, dated Jul. 8, 2008.
ATCC No. 40579 Product Sheet, Designation IMC01, page retrieved Apr. 30, 2014.
ATCC No. 40811 Product Sheet, Designation A129.5, derived from ethyl methanesulfonate mutants of cv. Westar, page retrieved Apr. 30, 2014.
ATCC No. 40812 Product Sheet, Designation A133.1, derived from ethyl methanesulfonate mutants of cv. Westar, page retrieved Apr. 30, 2014.
ATCC No. 75025 Product Sheet, Designation M3062.8, derived from ethyl methanesulfonate mutants of cv. Westar, page retrieved Apr. 30, 2014.
ATCC No. 75446 Product Sheet, Designation IMC130, derived from a cross of IMC129 x IMC01, page retrieved Apr. 29, 2014.
ATCC No. 75560 Product Sheet, Designation AG019, derived from a cross of AG013 x BN0010, 1999.
Burns et al., "QTL analysis of an intervarietal set of substitution lines in *Brassica napus*: (i) Seed oil content and fatty acid composition," Heredity (2003) 90. pp. 39-48.
Chen et al., Fatty acid inheritance in microspore-derived populations of spring rapeseed (*Brassica napus* L.) Theor Appl Genet (1990) 80: pp. 465-469.
Chen & Gertsson, "Genotypes for High Oleic Acid Content (about 80%) in the Oil of Rapeseed (*Brassica napus* L.)" Curciferae Newsletter No. 13, Nov. 1988, pp. 46-47.
Diepenbrock and Wilson, "Genetic Regulation of Linolenic Acid Concentration in Rapeseed" Crop Sci vol. 27 (1987) pp. 75-77.
Downey, R.K., "*Brassica* oilseed breeding—achievements and opportunities" Plant Breeding Abstracts, vol. 60, No. 10, (1990) pp. 1165-1170.
English et al., "Potential for High Oleic/Low Linolenic Canola for Australia" 12th Australian Research Assembly on *Brassicas*, (2001) pp. 33-36.
GenBank Accession No. L26296 (ATHD12AAA) Okuley et al., "*Arabidopsis* FAD2 gene encodes the enzyme that is essential for polyunsaturated lipid syntheses" www.ncbi.nlm.nih.gov/nuccore/L26296, accessed on Apr. 30, 2014.
GenBank Accession No. AF243045 (*Brassica napus*) Katavic et al., "Isolation and Characterization of Full-length cDNA Clone Encoding a *Brassica napus* Endoplamic Reticulum-bound Delta 12 Oleate Desaturase (FAD2)" www.ncbi.nlm.nih.gov/nuccore/AF243045, accessed on Apr. 29, 2014.
Hu et al., "Generation of DNA-based Markers in Specific Genome Regions by Two-primer RAPD Reactions" Genome Res. J, vol. 4 pp. 346-351, 1995.
Kirk and Oram, "Isolation of Erucic Acid-free Lines of *Brassica juncea*: Indian Mustard Now a Potential Oilseed Crop in Australia" J. Aust. Institute Agricultrual Science vol. 47, (1981) pp. 51-52.
Liu et al., "Genetic modification of cotton seed oil using inverted-repeat gene-silencing techniques" Biochem Soc Trans. vol. 28 (2000) pp. 297-29.
Mikolajczyk et al., "Allele-specific SNP markers for the new low linolenic mutant genotype of winter oilseed rape" Plant Breeding vol. 129 (2010) pp. 502-507.
Oelke et al., "Minnesota Agricultural Experiment Station Variety Trials—Canola" Univ. of Minn., (1997).
Okuley et al., "*Arabidopsis* FAD2 Gene Encodes the Enzyme That Is Essential for Polyunsaturated Lipid Synthesis" The Plant Cell, vol. 6 (1994) pp. 174-158.
Pandian et al., "Reduction of nutritionally undesirable saturates in *Brassica napus* and *B. juncea* oils using post-transcriptional gene silencing" 13th Australian Research Assembly on *Brassicas*, (2003) pp. 87-89.
Phillips et al., "Managing the value of new-trait varieties in the canola supply chain in Canada," Univ. of Saskatchewan (2000).
Rakow et al., "Opportunities and Problems in Modification of Leveles of Rapeseed C18 Unsaturated Fatty Acids" J. Am. Oilseed Chemists 50 (1973) pp. 400-403.
Robbelen et al., "Genetical and Physiological Investigations on Mutants for Polyenoic Fatty Acids in Rapeseed" vol. 75 (1975) pp. 93-105.
Roy et al., IXLIN—an interspecific Source for High Linoleic and Low Linolenic Acid Content in Rapeseed (*Brassica napus* L.) vol. 95 (1985) pp. 201-209.
Roy and Tarr, "Prospects for the Development of Rapeseed (*B napus* L.) with Improved Linoleic and Linolenic Acid Content" Plant Breeding vol. 98 (1987) pp. 89-96.
Rucker et al., "Development of high oleic rapeseed" Proceedings of the 9th International Rapeseed Congress, Cambridge, UK, (1995) pp. 389-391.
Salisbury et al., "Breeding for functional foods" 13th Australian Research Assembly on *Brassicas*, (2003) pp. 90-92.

(56) References Cited

OTHER PUBLICATIONS

Scarth et al., "Apollo low linolenic summer rape" Can. J. Sci., vol. 75, (1995) pp. 203-204.

Scarth et al., "Breeding for Special Oil Quality in Canola/Rapeseed" 8th GCIRC international Rapeseed Congress, Univ. of Manitoba, CA (1991).

Scarth et al., "Stellar Low Linolenic-High Linoleic Acid Summer Rape" Can. J. Plant Sci. vol. 68 (1988) pp. 509-511.

Schierholt et al., "Genetic and Environmental Variability of High Oleic Acid Content in Winter Oilseed Rape" GCIRC 1999 International Rapeseed Congress, Canberra AU (1999).

Smyth and Phillips, "Identity-preserving production and marketing systems in the global agri-food market: Implications for Canada" Aug. 2001, pp. 1-79.

Stoutjeskijk et al., "High-oleic acid Australian *Brassica napus* and *B. juncea* varieties produced by co-suppression of endogenous $\Delta 12$-desaturases" Biochemical Society Transactions, vol. 28, part 6 (2000), pp. 938-940.

U, Nagaharu, "Genome-analysis in *Brassica* with special reference to the experimental formation of *B. napus* and peculiar mode of fertilization" Jap. J. Bot. vol. 7 (1935), pp. 389-452.

Wong al. "The development of high oleic canola" 8th GCIRC International Rapeseed Congress, Saskatoon, CA, (1991), p. 207.

Registration details of Apollo variety from Agriculture Canada, Reg. No. 2816, 1987.

Registration details of Stellar variety from Agriculture Canada, Reg. No. 3694, 1993.

Scarth et al., "*Brassica* oils. Designer canola—a review of new food grade oils with a focus on high oleic, low linolenic types" 10th International Rapeseed Congress, (1999) Canberra, 7 pp.

* cited by examiner

```
  1 C  TCCCTCGCTCTTTCTCCTACCTCATCTGGGACATCATCATAGCCTCC  50
    | ||| ::,.. ||| ' ||| || ||||| ||| ||| || ||| |||| ! ||| ||!:;|||| ;
  1 C  .TCCC?CGCTCTTTCTCCTACCTCATCTGGGACATCATC TAGCCTCC  50

51 TGCTTCTACTACGTCGCCACCACTTACTTCCCTCTCCTCCCTCACCCTCT  100
    :||||! < ! ||| |||||| ||||||||||||||!|||||||||||!:!!!!
 51 TGCTTC  CTACGTCGCCACCACTTACTTCCCTCTCCTCCCTCACCCTCT  100

101 CTCCTAC TCGCCTGGCCTCTCTACTGGGCCTGCCAGGGCTGCGTCCT     150
    : ! :  .   ,.:!|!;||!:|;  !!;!|||||!||||||||!,!!':.
101 CTCC7AC77CGCCTGGCC  CTCTACTGGGCCTGCCAGGGCTGCGTCCT .  150

151 C GGC37 7GGG7CATAGCCC  CG GTGCGGCCACCACGCCT7:  GC A2 :00
    .''.  .   !:!.;:!:: !,..!!!!|||!:,||||,,!::
151 CCGGCG7C7GGGTC.::l... TAGCCCll.CGAGTGCGGCCACCACGCCT";C;:..GC3;..2 ::80

201 TACCAG7GGCTGGACGACACCGTCGGCCTCATCTTCCACTCC 7CCTCC7 ::80
    ,.!..  :||!|; |||||!|||||||  !|||||||||:!:.,j;:;:'.
201  ACCAG7GGCTGGACGACACCGTCGGCCTCATCTTCCACTCC77CC7CC'; ::80

251 CGTCCC  TACTTCTCCTGQ  GTACAGTCATCGACGCCACCA7TCC  c;,  300
    .,,,!::  .:!;:!||||||!|||||||!|||||||||||  !.;:!;;
251 CGTCCC': ACTTCTCCTGGAAGTACAGTCATCGACGCCACCATTCC   CA  300

301 CTGGCTCCCTCGAGAGAGACGAAGTGTTTGTCCCCAAGAAG  TCAGAC  350
    !!!!!;■||||||||||||||||||||||||||||||||||;!!||
301 CTGGCTCCCTCGAGAGAGACGAAGTGTTTGTCCCCAAGAAG ::l...GTCAGAC 350
                                              . Forward
351 ATCAAGTGGTACGGCAAGTACCTCAACAACCCTTTGGGACGCACCGTGAT  400
    !||||||;!!||||||||  |||111111 ||| || ||| |||||!||||!!!!|!;
351 ATCAAGTGGTACGGCAAGTACCTCAACAACCCTTTGGGACGCACCGTGAT  400
         primer   T
401 GTTAACGG  TAGTTCACTCTCGGCTGGCCTTTGTACTTAGCCTTCAAG  450
         !!i|i::;i;|  |||!|||!||||!!|||/!|||||!!!!!!cl|||;|
401 GTTAACGGTTCAGTTCACTCTCGGCTGGCCTTTGTACTTAGCCTTCAACG  450

451 TCTCGGGGAGACCTTACGACGGCGGCTTCGCTTGCCATTTCCACCCC?-C  500
     /|||||!|||!111111 |||||||||| |||||||||||||!:|||||||
451 TCTCGGGGAGACCTTACGACGGCGGCTTCGCTTGCCATTTCCACCCC.C  500

501 GCTCCCATCTACAACGACCGTGAGCGTCTCCAGATATACATCTCCGACGC  550
    ||||||||!||||||||||||||||||| ||||||||||| ||!|||||
501 GCTCCCATCTACAACGACCGTGAGCGTCTCCAGATATACATCTCCGACGC  550

551 TGGCATCCTCGCCGTCTGCTACGGTCTCTACCGCTACGCTGCTGTCCAAG  600
    |||||||!|!|!|||| |||!||||||| ||| || ||| |||||||||| || !!: ||||||
551 TGGCATCCTCGCCGTCTGCTACGGTCTCTACCGCTACGCTGCTGTCCAAG  600
```

Fig. 1

```
601 GAGTTGCCTCGATGGTCTGCTTCTACGGAGTTCCTCTTCTGATTGTCAAC 650
    |!;||:|  !||||i|||||||||||||||||||||!||i:|||:||||!;
601 GAGTTGCCTCGATGGTCTGCTTCTACGGAGTTCCTCTTCTGATTGTC  .C 650

651 GGGTTCTTAGTTTTGATCACTTACTTGCAGCACACGCATCCTTCCCTGCC 700
    |i:i!!|;|||||||||||||!|||||||||||!!||||!||'||||i|.
651 GGGTTCTTAGTTTTGATCACTTACTTGCAGCACACGCATCCTTCCCTGCC 700

701 TCACTATGACTCGTCTGAGTGGGATTGGTTGAGGGGAGCTTTGGCCACC3 750
    , ;i,,.;/|i':|||||  ||||||||,|i||||i;:||:;.,;|||:;
70: TCACTA GACTCGTCTGAGTGGGATTGGTTGAGGGGAGCT TGGCCACCG 750

751 TTGACAGAGACTACGGAriTCTTG  C GGTCTTCCAC TATCACGGAC  800
    \!;i;||.'|,'',,r|,;i|.| |;|||...,r|!|r   ;r'  ii',;
75: 7TGACAGAGACTACGG  TC7TGAA£.  GTCTTCCAC TATCACGGAC 800
       Reverse primer
801 GCACGTGGCGCATCACCTGTTCTCGACCATGCCGCATTATCATGCGA850
    ;.,:|i,, |, |||:: |||,|||;,|' |,|||||',|||*!,,,,,, ,,,|,,,,
801 ACGCACGTGGCGCATCACCTGTTCTCGACCATGCCGCATTATCATGCGA850

851 GG - GCTACG - GGCGAT  GCCGATACTGGGAGAGTATTATCAGTTCG  900
    |i!|i!;:|||!!|||||||||||||||||||||||i|i|!  :: |||i|,
851 GGAAGCTACGAAGGCGATAAAGCCGATACTGGGAGAGTATTATCAGTTCG 900

901 ATGGGACGCCGGTGGTTAAGGCGATGTGGAGGGAGGCGF GGAGTGTATC 950
    ||!||||i;|||||||||||i|! ||||||||||||||||||||!!||.|i!|||
901 ATGGGACGCCGGTGGTTAAGGCGATGTGGAGGGAGGCGAAGG GTGTATC 950

951 TATGTGGAACCGGACAGGGAAGGTGACk GAAAGG 985
    |||||||||||!|||||!|||||||||||||||||||
9S1 TATGTGGAACCGGACAGGGAAGGTGAC. GAAAGG 985
```

Fig. 1 Cont.

```
                  1                                                        50
DMS100    ---------- ---------- ---------- ---------- ----------IP
Quantum   ---------- ---------- ---------- ---------- ----------IP
Bn.Fad2   MGAGGRMQVS PPSKK3E:"DT IKRVPCE:"PP :=TVGELKK.;i PPHC: K- SIP 51                                                       100
DMS100    RS :-S":."LI;:DI  I IASc::o:::-vA TT- :::PLLPHP LS:;:_:-pL:.:  <.CQGCVL:"GV
Quantum   RS::s::LI',,JDII L .SC ::":"VA TT":-:::PLLPHP L2 -:-:....PL'(:: :,.CQG-:'VL-:-GV
Bnfad2    ?..s::S':·Lr-::oi I r.:;sc:--:-:·v;,. :- -.-=:PLLPHP L-::-:..."PL-::: _.:.QG.:.:V-:G 101                                                       :.50
DMs :00   -:v:;_.:-:EE':GHH ?_:2:D .:Q:. LDD ":"VGLI :.-E-:3.-=L LVP.  _  ":-S  H:?::EE-: :--3 =:
Qt..a:::cum:  ::VL .HE :'GmH  E.::;o Q-:"LDD -::-VGLI .I-:3.=L LVP-.     .r.- H?_?.H :; r:G
3nfad2    -vr.::: _HE-:-GHH A .:;o Q.LDD ':VGLI::-:2_I-L LVP-..,-=  K...-s H?H:-:=: I-:G::
                                                                 T
                151                                                       200
DMS100    LERDEV?VPK KK.3DI?C:-GK ...:"LNNPLG:<.:V ML:V* :::LG:;  PL:L.:..."V.3G
Quantum   LERDEV:-VPK KKSDI!-G·:·:GK :::-LNNPLGR-V ML-VQ..:.-LG -i PL":.L.:_ NVSG
BNfad2    LERDEV:?VPK KKSDII(">7::GK :::-LNNPLG?.:V ML!'VQ ?:'LG'i PL- L.I'..-i-JV.3G 201                                                       250
DMS:00    RP -."DGG:;. CH ?HPNAP I :-ND RERLQI ".'ISD AGII.:...V: ::GL -R:: ?:...VQGVA
Quantum   RP":.DGG:::-ACH ?HPNAPI"YND RERLQI -i-ISD AGII.;,.VC":."GL :-R':-::-.VQGVA
BNfad2    RP':DGG?ACH 7HPN.il.P I ':"ND RERLQI' I:3D //.GIkI.V-:::GL :-R':.iI_ .QGVA 251                                                       300
DMS100    SMVC::"!GVPL LIVNG?LVLI T:.:"LQHTHPSL PHYDSSE:-iDfl:-1 LRGAL.:"VDR
Quantum   SMVC?"!GVPL LIVNG?LVLI '!""LQHTHPSL PH':..IJSSE JD"I{\1 LRG. .::\.VDR
BNfad2    SMVC?::GVPL LIVNGLLVLI T::"LQH HPSL PH":DSSE ;m-J LRGALA:VDR 301                                                       350
DMS100    D'.:"GILNh.'V?H NITDTHVAHH L?STMPH"..."H..I\ MEA':'K.:,.I KP I LGE":'.:"Q ?DGT
Quantum   DYGILNh.'V?H NITDTHVAHH L?STMPH":.:X<\. MEA':'K.:,IKPI LGE":::::Q?DGT
BNfad2    DYGILNKV?H NITDTHViI.IHH Li?STMPH':.:H. MEATKAIKPI LGE'!-Q?DGT 351                 384
DMS100    PWKAM'!iñ.EA KECI:':'VEPDR EGDKK-----
Quantum   PVVKAMviREA KECI'"!VEPDR EGDKK-----
BNfad2    PWIOL.MliiREA KECI?!VEPDR QGEKKGV:? !"'Y NNKL
```

Fig. 2

```
                Forward primer
  1 CAAGAATTTGTCCCACAGTACACGGATGCTCAGATACACTGTCCCTCTCC  50
    :!!!!i!!!!!!i;!i!!!!!i i!!!!!!!!!!!!!!!!!!!!!!!!!!
  1 CAAG ATTTGTCCCACAGTACACGGATGCTCAGATACACTGTCCCTCTCC  50    Exon 4

51 CCATGCTCGCTTACCCTCTCTATCT CGTA  CCTPATTCCTk TTTTTC  100
    !!!!:!ii!!!!;!!!!!!!!i!!! !! !!!!!!!!!i!!!!!!!!!!:
 51 CCATGC CGCTTACCCTCTCTATCT CGT  JCCTAATTCCT  TTTTTC  100

101 TTCCTGATTAT ATTACAATTTTGAATTTTT GATTTTGAGTATTPACTA  150    Intron 4
    !!!!!!!!1111 i!!!!!! !!!!!! !!! !!!!! !!!!!!!!!!!!!
101 TTCCTGATTATAATTACAP TTTGAATTTTTAGATTTTGAGTATTAACTA  150

151 -TAT - TT -TTTGTTTGGGGATGACTACAG GGTACAG   TCCTC    200
    !!!:;. !!!!!:;!!! !!!!!!!! !!!!!!! !!!!!!!!!!!:!!·
151  TA -    -TT -TTTGTTTGGGGATGACTACAG GGTACAG  GTCCT  ...180

20 GT.   - GGGT  C TT T  CCCAT C GLAGTTTATTLGCC CAAGC  250
    ! :·:  : ::  '  .: !·::;!!! ==:· ! !; J ;: ·7.
201 GT  G  GGGTC  C T AT   CCCATACAGTAGTTTATTTGCCCC AGC  250

251 GAGAG;.;.Jl..GCTT.il.TTGCA.:!,.CTIC;....D.CTACTGCTGGTCGATCGTGTGGC 300
    !j!!!i!!!!!!!l,i;!i!!;!!!!!!; !!!;!!!! !!!!! !!::.!ii:.
:151 G.il.GAGA..E... GCTATTGCAACTTCAACT.:1,.CTTGCTGGTCGATCGTGTTGGC 300      Exon 5

301 CTCFTGTTTATCTATCATTCCTCGTTGGTCCAGTCACAGTTCTAF- G  350
    !!:·:i:!!!!!;;!!!!!!!!!!!!!!! !3!!!!!!!!!!!:.i!!;!
301 CACTCTTGTTTATCTATCATTCCTCGTTGGTCCAGTCACAGTTCT   -G  350

351 TCTATGGTGTTCCTTACAT TA.D.GTTTCATATATTTCTTTATTATATCA 400
    !!!!!!!!!!!!!!!!!!!!!!!!!!!!!!!!!!!!!!!!!!!!,!!!!!!:
351 TCTA GGTGTTCCTTACAT  TAAGTTTCATATATTTCTTTATTATATCA 00   Intron 5

401 TTGCTAATATAATTTGTTTTTGACATAAAAGTTTTGGP TTTCAGAT  450
    !!!!!!!!!!!!!!!!!!!!!!!!!; !!!!Jiil!!!!!!!!!!!!!111111
401 TTGCTAATATAATTTGTTTTTGACATAAAAGTTTTGGAAAAATTTCAGAT 450

451 CTTTGTAATGTGGTTGGACGCTGTCACGTACTTGCATCATCATGGTCACG SAO
    ii!!!!!!!!!!!!!!!! !!! 111111 !!!!!!!1111111 !!!!!!!!!!
451 CTTTGTAATGTGGTTGGACGCTGTCACGTACTTGCATCATCATGGTCACG 500    Exon 6
                                              Reverse primer
501 ATGATAAGCTGCCTTGGTACAGAGGCAACATAAGTAGATCAACATTATTT 550
    !!·!!!!!!!!!!!!!!!!!!!!!!!!!!!!!!! ii!!!!!!!!!!!!!!!!!i
501 ATGATAAGCTGCCTTGGTACAGAGGCAACGTAAGTAGATCAACATTATTT 550

551 ATAAGkD.GCAATAATGATTAGTAGTTGAATAATCTGAATTTTTGATGTTT 600    Intron 6
    -!!!!!!!!!1111!!!!!!!!!!!!!!!!!!!!!!!!!!!!!!!!!!!!!!
551 ATAAGAAGCAATAATGATTAGTAGTTGAATAATCTGAATTTTTGATGTTT 600

601 TTGTACAATAATACpAATGGAGTTATTTACGTGGAGGATTAACAACAGT 650     Exon 7
    !!!!!!!!!!!!!!!!!!!!!!!!!!!!!!!!!!!!!!!!!!!!!!!!:
601 TTGTACAATAATACpAATGGAGTTATTTACGTGGAGGATTAACAACAGT  650

Table 1.

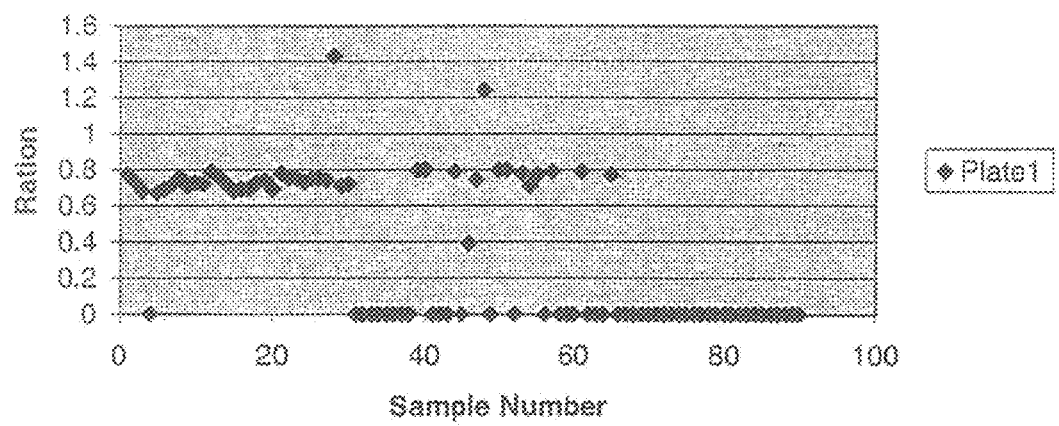
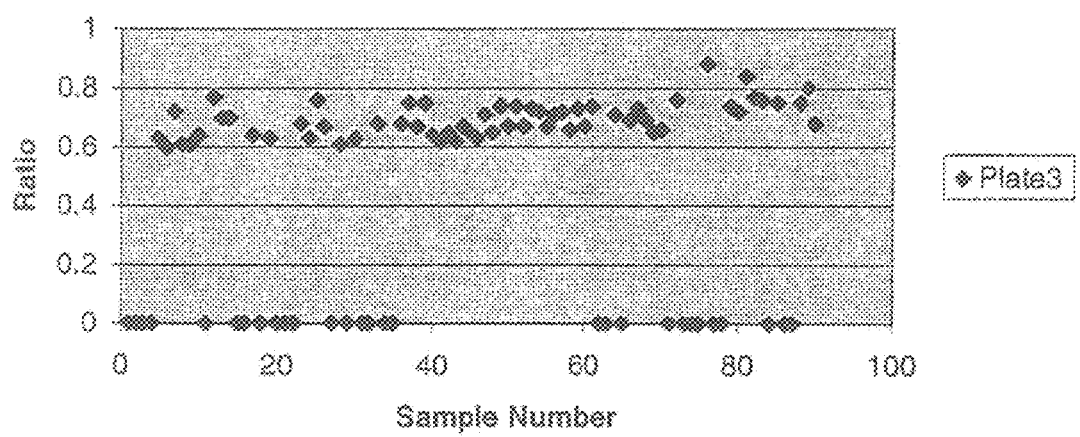
Fig. 6c

Fig. 7

ALTERED *FAD2* AND *FAD3* GENES IN *BRASSICA* AND THE MOLECULAR MARKER-ASSISTED DETECTION THEREOF

CROSS-REFERENCE TO RELATED APPLICATION

This application is a national phase entry under 35 U.S.C. §371 of International Patent Application PCT/US2004/003852, filed Feb. 11, 2004, published in English as International Patent Publication No. WO 2004/072259 on Aug. 26, 2004, which claims priority to U.S. Patent Application No. 60/446,429 filed Feb. 11, 2003, the entire contents of which is hereby incorporated herein by this reference.

TECHNICAL FIELD

The present invention relates generally to methods and materials for use in plant breeding. More specifically, the present invention relates to the marker-assisted identification of genes encoding phenotypic traits in oil seed plant species, and in *Brassica* species in particular.

BACKGROUND

The genus *Brassica* includes canola, one of the world's most important oilseed crops, and the most important oilseed crop grown in temperate geographies. Canola has been traditionally characterized as *Brassica napus* (a species derived as a result of inter-specific crosses of *Brassica rapa* and *Brassica oleracea*) in which erucic acid and glucosinolates have been eliminated or significantly reduced through conventional breeding. The majority of canola oil is in the form of vegetable oils produced for human consumption. There is also a growing market for the use of canola oil in industrial applications.

Canola is a polyploid species considered to have arisen from the hybridization of *Brassica oleracea*, having a diploid C genome, and *Brassica rapa*, having a diploid A genome. Cytogenetic investigation revealed the AA and CC genomes show a degree of relatedness, being partially homologous to one another and thought to have been derived from a common ancestor genome (Prakash and Hinata, 1980). Although technically classified as diploids, the genomes of both progenitor species contain a high percentage of regions duplicative of one another (Song et al., 1991). Genetic analysis revealed that the AA genome of *Brassica rapa* contributed ten chromosomes to *Brassica napus*, while *Brassica oleracea* contributed nine chromosomes from its CC genome as the maternal donor (Song et al., 1992).

The quality of edible and industrial oil derived from a particular variety of canola seed is determined by its constituent fatty acids, as the type and amount of fatty acid unsaturation have implications for both dietary and industrial applications. Conventional canola oil contains about 60% oleic acid (C18:1), 20% linoleic acid (C18:2) and 10% linolenic acid (18:3). The levels of polyunsaturated linolenic acid typical of conventional canola are undesirable as the oil is easily oxidized, the rate of oxidation being affected by several factors, including the presence of oxygen, exposure to light and heat, and the presence of native or added antioxidants and pro-oxidants in the oil. Oxidation causes off-flavors and rancidity as a result of repeated frying (induced oxidation) or storage for a prolonged period (auto-oxidation). Oxidation may also alter the lubricative and viscous properties of canola oil.

Oils exhibiting reduced levels of polyunsaturated fatty acids and increases in the level of monounsaturated oleic acid relative to conventional canola oil are associated with higher oxidative stability. The susceptibility of individual fatty acids to oxidation is dependent on their degree of unsaturation. Thus, the rate of oxidation of linolenic acid, which possesses three carbon-carbon double bonds, is 25 times that of oleic acid, which has only one double bond, and two times that of linoleic acid, which has two double bonds. Linoleic and linolenic acids also have the most impact on flavor and odor because they readily form hydroperoxides. High oleic oil ($\geq$70% oleic) is less susceptible to oxidation during storage, frying and refining, and can be heated to a higher temperature without smoking, making it more suitable as cooking oil.

Two strategies are generally used to increase the oxidative stability of canola oil. In one approach, partial hydrogenation is used to lower linolenic acid content. Unfortunately, partial hydrogenation leads to the formation of trans-fatty acids, which have been linked to elevated levels of low-density lipoprotein cholesterol (LDL or "bad" cholesterol) in the blood, and consequently, to an increased risk of coronary heart disease. The second major strategy involves breeding programs to develop canola varieties with high oleic and low linolenic acid levels relative to conventional canola oil. High oleic and low linolenic mutants have been produced through mutagenesis (Rakow, 1973; Wong et al., 1991; Auld et al., 1992) and transgenic modification (Debonte and Hitz, 1996). Examples of commercially sold canola varieties having a fatty acid profile of C18:1 above 70% and C18:3 below 3.5% are the Nexera™ varieties, marketed by Dow AgroSciences LLC (Indianapolis, Ind.), which varieties produce Natreon™ oil. One such line, AG019 (a Nexera™ variety) contains 71% to 78% oleic (C18:1) and <3% linolenic (C18:3) acid. AG019 was originally created by ethyl methanesulphonate (EMS) mutagenesis and is described in U.S. Pat. No. 6,169,190 B1 to Sernyk, assigned to the assignee of the present invention.

Current methods for producing $F_1$ hybrid *Brassica* seeds have definite limitations in terms of cost and seed purity. Generally, these methods require stable, sib-incompatible and self-incompatible, nearly homozygous parental breeding lines, which parental breeding lines are available only after repeated selfing to generate inbred lines. Furthermore, inbreeding to develop and maintain the parental lines is accomplished by labor-intensive techniques, such as bud pollination, since *Brassica* hybrid seed production systems based on self-incompatible traits must utilize strongly self-incompatible plants. Environmental conditions during the breeding process, such as temperature and moisture, typically affect plant lipid metabolism, thus also affecting the content level of fatty acids (Harwood, 1999). Environmental variability, therefore, makes the phenotypic selection of plants less reliable. Deng and Scarth (1998) found that increase in post-flowering temperature significantly reduced the levels of C18:3 and increased C18:1. Similar results were reported in other studies (Yermanos and Goodin, 1965; Canvin, 1965).

Breeding for low linolenic varieties is particularly challenging since C18:3 content is a multi-gene trait and inherited in a recessive manner with a relatively low heritability. Genetic analysis of a population derived from the cross between "Stellar" (having a low C18:3 content (3%)) and "Drakkar" (having a "conventional" C18:3 level (9% to 10%)) indicated that the low C18:3 trait was controlled by two major loci with additive effects designated L1 and L2 (Jourdren et al., 1996b). These two major loci controlling C18:3 content were found to correspond to two fad3 (fatty acid desaturase 3) genes; one located on A genome (originating from *Brassica rapa*) and the other on the C genome (originating from *Brassica oleracea*) (Jourdren et al., 1996; Barret et al., 1999).

Traits that are continuously varying due to genetic (additive, dominance, and epistatic) and environmental influences are commonly referred to as "quantitative traits." Quantitative traits may be distinguished from "qualitative" or "discrete" traits on the basis of two factors: environmental influences on gene expression that produce a continuous distribution of phenotypes; and the complex segregation pattern produced by multigenic inheritance. The identification of one or more regions of the genome linked to the expression of a quantitative trait led to the discovery of Quantitative Trait Loci ("QTL"). Thormann et al. (1996) mapped two QTL that explained 60% of the variance for the linolenic content, while Somers et al. (1998) identified three QTL that collectively explained 51% of the phenotypic variation of C18:3 content. A three-locus additive model was also reported by Chen and Beversdorf (1990). Rücker and Röbbelen (1996) indicated that several minor genes are most likely involved in the desaturation step.

Heritability for C18:3 content was estimated to be 26% to 59% (Kondra and Thomas, 1975) (where the variability of heritability is a function of genetics as opposed to environmental factors). Complexity of the inheritance of linolenic acid may be due to the fact that linolenic acid can be synthesized either from the desaturation of C18:2 or the elongation of C16:3 (Thompson, 1983).

In contrast to linolenic acid, inheritance of oleic acid is less complex, and the heritability of oleic acid is relatively high. It is reported that high oleic acid content is controlled by a major locus called fad2 (fatty acid desaturase 2) gene which encodes the enzyme responsible for the desaturation of oleic acid to linoleic acid (C18:2) (Tanhuanpaa et al., 1998; Schierholt et al., 2001). All of the functional gene copies of the fad2 gene that have been reported and mapped to date are located on the A-genome-originated linkage group N5 (Scheffler et al., 1997; Schierholt et al., 2000). Chen and Beversdorf (1990) reported that the accumulation of oleic acid was controlled by at least two segregation genetic systems, one acting on chain elongation and the other involving desaturation. Heritability for C18:1 content was estimated to be 53% to 78% (Kondra and Thomas 1975) and 94% (Schierholt and Becker, 1999), respectively. Due to the higher heritability, the expression of C18:1 content is environmentally less affected and relatively stable (Schierholt and Becker, 1999).

In Nexera™ canola germplasm, one to two genes are found to control C18:1 content and at least three genes are involved in C18:3 expression. In segregating progenies, the distribution of seed C18:3 content is continuous, thereby making it difficult to identify genotypic classes with desirable C18:3 levels. In addition, there is a low correlation in fatty acid content between greenhouse (GH) and field-grown plants, further making it challenging to reliably select GH plants with desirable levels of C18:3.

Molecular maker selection is based on genotypes and is, therefore, independent from environmental effects. Molecular markers would alleviate the problem of the unreliable selection of plants in the greenhouse attributable to the low correlation in fatty acid content between greenhouse-grown plants and field-grown plants. Significantly, molecular markers tightly linked to the genes controlling C18:1 and C18:3 content would allow early selection of plants carrying genes for high C18:1 and low C18:3. Marker-assisted selection at early stage will significantly save greenhouse space, therefore, improve the efficiency of greenhouse use, and reduce the breeding workload in the field.

More generally, molecular markers have advantages over morphological markers in that: molecular markers can be highly polymorphic while morphological markers are strictly phenotype dependent; morphological markers may interfere in the scoring of certain quantitative phenotypes while molecular markers exhibit a 1:1 relationship between genotype and phenotype (thus allowing the unambiguous scoring of all possible genotypes for a given locus); and epistatic interactions tend to limit the number of morphological markers useful in a population, while molecular markers do not interact epistatically.

Different types of molecular markers such as RAPD (random-amplified polymorphic DNA) markers (Tanhuanpaa et al., 1995; Hu et al., 1995; Rajcan et al., 1999; Jourdren et al., 1996), RFLP (restriction fragment length polymorphism) markers (Thormann et al., 1996) and SCAR (sequence-characterized amplified region) markers (Hu et al., 1999) have been identified to be associated with low C18:3 levels in *Brassica napus*. Molecular markers have also been identified for high C18:1 content. A RAPD marker was identified to be linked to the QTL affecting oleic acid concentration in spring turnip rape (*B. rapa* ssp. *oleifera*) and was later converted into a SCAR marker (Tanhuanpaa et al., 1996). Schierholt et al. (2000) identified three AFLP markers linked to a high oleic acid mutation in winter oilseed rape (*B. napus* L.). Tanhuanpaa et al. (1998) developed an allele-specific PCR marker for oleic acid by comparing the wild-type and high-oleic allele of the fad2 gene locus in spring turnip rape (*B. rapa* ssp. *oleifera*). However, most of these markers are low-throughput markers, such as RAPD, AFLP and RFLP, and are not suitable for large-scale screening through automation.

Therefore, what is needed in the art are molecular markers suitable for identifying canola plants producing a seed oil with desired levels of high oleic and low linolenic acid, which render the oil sufficiently stable for uses in various dietary and industrial applications. It would be further advantageous to map genes responsible for oleic and linolenic acid concentration and to develop high throughput PCR markers linked to high oleic and low linolenic acid content in order to facilitate the selection of these traits in oil seed crop trait introgression and breeding.

SUMMARY OF THE INVENTION

The present invention provides methods of marker-assisted selection in canola and other oil seed crop species, as well as isolated nucleic acids for use as molecular markers in such methods.

In a first embodiment, an isolated and purified genetic marker associated with high oleic oil content in *Brassica* is provided. The marker maps to a linkage group selected from the group consisting of N5 and N1 in the *Brassica* genome, and has the sequence of SEQ ID NO. 5 or a derivative thereof. An isolated and purified genetic marker associated with low linolenic oil content in *Brassica* is also provided. The marker maps to a linkage group selected from the group consisting of N14 and N4 in the *Brassica* genome, and has the sequence of SEQ ID NO. 6 or a derivative thereof.

In another embodiment, the present invention provides nucleic acid sequences corresponding to mutated fad2 and/or fad3 genes. These genes may be introduced into canola or other oil seed plants by any of a number of known methods in the art. Additionally, wild-type fad2 and/or fad3 may be altered by known in vivo or in vitro methods to correspond to the fad2 and/or fad3 genes of the present invention.

In an additional embodiment, molecular markers corresponding to the fad2 and fad3 gene mutations are disclosed.

The markers of the present invention are highly useful for the direct selection of desirable fad2 and fad3 alleles during marker-assisted trait introgression and breeding. In one aspect of the embodiment, two single nucleotide polymorphism (SNP) markers are provided that correspond to the alleles. Thus, the present invention advantageously permits one of skill in the art to breed for the molecular markers described herein, or derivatives thereof, rather than breeding for the phenotype. In a related embodiment, methods of marker-assisted selection for high oleic and/or low linolenic oil seed plants are disclosed. In one aspect of the embodiment, methods for reliably and predictably introgressing traits for high oleic and/or low linolenic acid content into Brassica germplasm are provided. The methods include: (a) identifying one or more nucleic acid markers for marker-assisted selection among Brassica lines to be used in a Brassica breeding program, wherein the nucleic acid markers map to at least one of linkage groups N14, N4, N5 or NI and wherein the nucleic acid markers are selected from among any of SEQ. ID. NOs. 5 and 6, and (b) introgressing the traits for high oleic and/or low linolenic acid content into Brassica by performing marker-assisted selection. A further method is drawn to identifying nucleic acid as a modulator of high oleic and/or low linolenic acid content in Brassica, and comprises exposing Brassica nucleic acid to a molecular marker selected from the group consisting of SEQ. ID. Nos. 5 and/or 6.

BRIEF DESCRIPTION OF THE FIGURES

FIG. 1 shows partial genomic nucleotide sequences of the fad2 gene cloned from DMS100 and Quantum. The top is DMS100 sequence (SEQ. ID. NO. 7) and bottom is Quantum sequence (SEQ. ID. NO. 9). The arrowhead indicates a single nucleotide mutation of C to T, which resulted in a stop codon (TAG) (shaded). The forward and reverse primers for PCR-based mutant allele-specific marker are bolded and underlined.

FIG. 2 provides amino acid sequences of the fad2 gene, degenerated from the genomic nucleotide sequence cloned from DMS100 (SEQ. ID. NO. 8), Quantum (SEQ. ID. NO. 10) and from a published Brassica napus fad2 gene (BNfad2) (SEQ. ID. NO. 11). The arrowhead indicates the position of the stop codon resulting from a single nucleotide mutation (C to T) in DMS100.

FIG. 3 shows genomic nucleotide sequences of the fad3c gene cloned from DMS100 and Quantum. The top is the DMS100 sequence (SEQ. ID. NO. 12) and the bottom is the Quantum sequence (SEQ. ID. NO. 13). Exons are boxed, introns are unboxed, which correspond to exons 4, 5, 6 and 7 and introns 4, 5 and 6 of the fad3 gene in Brassica rapa and Arabidopsis. The arrowhead indicates a single nucleotide mutation of G to A. The forward and reverse primers for PCR-based mutant allele-specific markers are bolded and underlined.

FIGS. 7 and 8 provide a list of the various PCR markers developed and tested for high oleic and/or low linolenic trait identification.

DETAILED DESCRIPTION OF THE PREFERRED EMBODIMENTS

Figure 4:
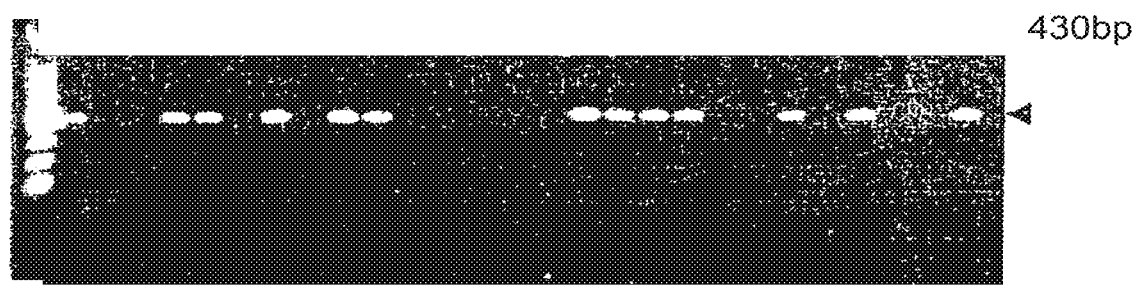
FIG. 4 provides a table that correlates the mutant allele-specific markers and fatty acid content of 184 DH lines derived from the cross of Quantum and DMS100, as well as electrophoresis results of PCR products amplified from the mutant allele-specific marker for the fad2 gene.

The present invention relates generally to methods and materials for use in plant breeding. In a preferred embodiment, the present invention relates to methods and compositions of matter for marker-assisted identification of genes encoding high oleic, low linolenic traits in canola.

By "genetic locus" is meant a location on a chromosome.

By "genomic locus" is meant a location within the entire set of chromosomes of an organism.

As used herein, "linkage disequilibrium" refers to a statistical association between two loci or between a trait and a marker.

As used herein, "marker" includes reference to a locus on a chromosome that serves to identify a unique position on the chromosome. A genotype may be defined by use of one or a plurality of markers.

The term "derivative," as used herein, refers to a modification of a sequence disclosed in the present invention. Illustrative of such modifications with regard to molecular markers would be the substitution, insertion, and/or deletion of one or more bases relating to a nucleic acid sequence of a marker disclosed herein that preserve, slightly alter, or increase the function of the molecular marker in identifying one or more high oleic and/or low linolenic traits in Brassica or other oil seed crop species. Such derivatives can be readily determined by one skilled in the art, for example, using computer modeling techniques for predicting and optimizing sequence structure. The term "derivative" thus also includes nucleic acid sequences having substantial sequence homology with the disclosed marker sequences herein such that they are able to have the disclosed functionalities for use in marker-assisted breeding.

The term "homology," as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence that lacks even a partial degree of complementarity (e.g., less than about 30% identity); in the absence of non-specific binding, the probe will not hybridize to the second non-complementary target sequence.

The terms "identity" and "similarity," as used herein and as known in the art, are relationships between two polypeptide sequences or two polynucleotide sequences, as determined by comparing the sequences. In the art, identity also means the degree of sequence relatedness between two polypeptide or two polynucleotide sequences as determined by the match between two strings of such sequences. Both identity and similarity can be readily calculated (*Computational Molecular Biology*, A. M. Lesk, ed., Oxford University Press, New York (1988); *Biocomputing: Informatics and Genome Projects*, D. W. Smith, ed., Academic Press, New York (1993); *Computer Analysis of Sequence Data, Part I*, A. M. Griffin and H. G. Griffin, eds., Humana Press, New Jersey (1994); *Sequence Analysis in Molecular Biology*, G. von Heinje, Academic Press (1987); and *Sequence Analysis Primer*, M. Gribskov and J. Devereux, eds., Stockton Press, New York (1991)). Methods commonly employed to determine identity or similarity between two sequences include, but are not limited to those disclosed in H. Carillo and D. Lipman, *SIAM J. Applied Math.* 48:1073 (1988). Preferred methods to determine identity are designed to give the largest match between the two sequences tested. Methods to determine identity and similarity are codified in computer programs. Typical computer program methods to determine identity and similarity between two sequences include: GCG program package (J. Devereux et al., *Nucleic Acids Research* 12 (1):387 (1984)), BLASTP, BLASTN, FASTA and TFASTA (S. F. Atschul et al., *J. Mol. Biol.* 215:403 (1990)).

An "insertion" or "addition," as used herein, refers to a change in an amino acid or nucleotide sequence resulting in the addition of one or more amino acid or nucleotide residues, respectively, as compared to the naturally occurring molecule.

The term "statistically associated" refers to the tendency of two events to occur together at a frequency greater than that attributable to chance, where the frequency attributable to chance is represented by a predetermined level of significance. Statistical association can be determined by any one of a number of significance tests well known to those in the art, for example, ANOVA or t-tests. See, e.g., *Statistical Methods*, G. W. Snedecor and W. G. Cochran, Iowa State University Press, Ames, Iowa (1985). Significance levels for alpha are preferably less than 0.01. For example, levels of significance for this invention could range between 0 and about 0.250, e.g., less than about 0.0001, 0.00050, 0.0010, 0.0050, 0.010, 0.025, 0.050, 0.100, or 0.250.

The term "stringency" is used herein to describe the conditions of temperature, ionic strength, and the presence of other compounds such as organic solvents, under which nucleic acid hybridizations are conducted. Those skilled in the art will recognize that "stringency" conditions may be altered by varying the parameters just described, either individually or in concert. With "high stringency" conditions, nucleic acid base pairing will occur only between nucleic acid fragments that have a high frequency of complementary base sequences (for example, hybridization under "high stringency" conditions may occur between homologs with about 85% to 100% identity, preferably about 70% to 100% identity). With medium stringency conditions, nucleic acid base pairing will occur between nucleic acids with an intermediate frequency of complementary base sequences (for example, hybridization under "medium stringency" conditions may occur between homologs with about 50% to 70% identity). Thus, conditions of "weak" or "low" stringency are often required with nucleic acids that are derived from organisms that are genetically diverse, as the frequency of complementary sequences is usually less.

As used in the present application, the term "substantial sequence homology" is used to indicate that a nucleotide sequence (in the case of DNA or RNA) or an amino acid sequence (in the case of a protein or polypeptide) exhibits substantial, functional or structural equivalence with another nucleotide or amino acid sequence. Any functional or structural differences between sequences having substantial sequence homology will be de minimis; that is, they will not affect the ability of the sequence to function as indicated in the present application. Sequences that have substantial sequence homology with the sequences disclosed herein are usually variants of the disclosed sequence, such as mutations, but may also be synthetic sequences.

A "substitution," as used herein, refers to the replacement of one or more amino acids or nucleotides by different amino acids or nucleotides, respectively.

Canola varieties DMS100 (mutant type) and Quantum (wild type) were used in the cloning of fad2 (fatty acid desaturase-2) and fad3 (fatty acid desaturase-3) alleles. The variety DMS100 was derived from an $F_4$ bulk of a single $F_3$ plant selection originating from the cross of Global×AG019 sister line. DMS100 is a HOLL (High Oleic and Low Linolenic) line with oleic acid content at about 77% and linolenic acid content at about 3%. Quantum is a commercial variety and contains low oleic acid (~66%) and high linolenic acid (~7%) content. As discussed in detail herein, sequencing of DMS100 genomic clones of fad2 and fad3 desaturase enzymes involved in the fatty acid synthesis pathway revealed single nucleotide mutations in each of the genes. Further sequence analyses show the mutations to be the cause of altered fatty acid contents in DMS100. These two mutations are distinct from previously published mutations (Tanhuanpää et al., 1998; Jourdren, 1996), and the use of these sequences as isolated nucleic acid conferring HOLL traits is an aspect of the present invention.

C18:1 content in canola is influenced by a fad2 gene that encodes an enzyme (endoplasmic delta 12 oleate desaturase) responsible for the desaturation of oleic acid (C18:1) to linoleic acid (C18:2). In the Examples that follow, nine DMS100 clones and ten Quantum clones were sequenced. The sequence analysis and alignment of these clones identified a single nucleotide mutation, C to T, at position 411 that consistently occurred in the fad2 gene sequence of all the DMS100 clones (SEQ. ID. NO. 7), but not the Quantum clones (SEQ. ID. NO. 9) (see FIG. 1). Further analysis indicated that this single nucleotide mutation occurred in the coding sequence (exon) of the fad2 gene (see FIG. 2). As further shown in FIG. 1, the mutation of C to T created a stop codon (TAG) that causes early termination of the polypeptide chain during translation. The stop codon results in the incorporation of only 185 amino acids into the polypeptide instead of all 384 amino acids of the full-length polypeptide (FIG. 2). The truncated polypeptide appears to have little, if any, function as an active desaturase for the desaturation of oleic acid to linoleic acid, thus leading to the accumulation of oleic acids in the seeds of the mutant line. The lack of functionality of the mutant fad2 gene explains the significantly higher C18:1 content (77%) of DMS100 relative to the wild-type line Quantum (66%).

The fad3 gene encodes for endoplasmic delta-15 linoleic desaturase, an enzyme responsible for the desaturation of linoleic acid (C18:2) to linolenic acid (C18:3). Two fad3 genes (fad31 and fad32) in particular have been reported to control linolenic content. Seven DMS100 clones and six Quantum clones of fad31 and six DMS100 clones and six Quantum clones of fad32 were sequenced. Sequence analysis and alignment revealed no sequence difference between DMS100 and Quantum clones for fad31 (data not shown). However, sequence alignment revealed a single nucleotide mutation, G to A, at the first base of 5' splice site of the third intron in fad32 gene (see FIG. 3). This intron corresponds to the intron 6 of the fad3 gene in *B. rapa* (Tanhuanpää, 2000) and *Arabidopsis* (Nishiuchi et al., 1994). The fad3 gene of *B.* rapa and *Arabidopsis* contains eight exons and seven introns, while the sequence examined covers exons 4 (partial), 5, 6 and 7 (partial) and introns 4, 5 and 6. This interpretation of exons/introns in the fad3 gene is supported by the fact that the fad3 gene sequence is highly conserved among sequenced *Brassica* species and *Arabidopsis*.

Plant introns contain highly conserved 5' splice sites (exon/intron junction—AG/GTAAG) and 3' splice sites (intron/exon junction—TGCAG/G. The first two nucleotides in the 5' splice site intron junction sequence, +1G and +2T, have shown 100% and 99% conservation, respectively, among over 1000 *Arabidopsis* introns studied (Lorkovic, 2000; and Brown, 1996). The accuracy of splicing depends on the mechanisms of intron signal recognition and the correct selection of 5' and 3' splice sites. Referring again to FIG. 3, the mutation of +1G to +1A at the 5' splice site (position 530) identified herein can abolish splicing or lead to exon skipping, i.e., the affected exon (exon 6) and both flanking introns are removed in a single splicing event (Lorkovic et al., 2000; Simpson et al., 1998). Such exon skipping could lead to synthesis of a polypeptide missing the amino acids encoded by the exon 6 of the fad3 gene. The mutation could also block splicing at the normal 5' splice site and activate cryptic splice sites at different positions, which can cause cryptic splicing of the affected exon together with the downstream intron (McCullough et al., 1993). Such cryptic splicing could lead early termination of translation and synthesis of a shorter polypeptide for delta-15 linoleate desaturase encoded by fad3. This will occur because the intron contains stop codons in all three possible reading frames and hence, exons 7 and 8 will remain untranslated. The incomplete translation of the fad3 can inactivate the enzyme and block the desaturation of linoleic acid (C18:2) to linolenic acid (C18:3), resulting in the decrease of C18:3 accumulation in canola seeds.

These data strongly suggest that the single nucleotide mutations identified in the fad2 and fad3 genes are factors that account for the increase in oleic acid and decrease in linolenic acid contents in the canola line DMS100. Using the molecular markers of the present invention or markers with substantial homology thereto, these two mutations may serve to allow marker-assisted introgression into canola lines making use of DMS100, its progeny or derivatives, or transgenic versions of its mutated fad2 and fad3 genes (SEQ. ID. NO. 7 (see FIG. 1) and SEQ. ID. NO. 12 (see FIG. 3), respectively), for purposes of developing HOLL canola.

Identification of Mutations in fad2 and fad3 Genes

Referring to FIG. 1, primers homologous to the *Arabidopsis* fad2 gene sequence were used to amplify genomic DNA fragments of the fad2 gene from *B. napus* lines DMS100 and Quantum. The primer pair FAD2-2F: CAATCCCTCGCTCTTTCTCCTACC (SEQ. ID. NO. 1) and FAD2-6R: CCTTTCTTGTCACCTTCCCTGTCC (SEQ. ID. NO. 2) amplified a fad2 fragment of the same length (986 bp) from each of the two parents. The amplified fragments were then cloned and sequenced to investigate the sequence differences of fad2 gene between the two parents.

Genomic DNA fragments corresponding to the fad31 and fad32 genes were amplified from DMS100 and Quantum lines using PCR. The primers for amplification were designed from the published *B. napus* fad31 and fad32 gene sequences (Brunel et al., 1999, GenBank Accession AF056569 and AF056570, respectively). The fad31 fragments amplified by the primer pairs BNFD31-CF (GAGGCTTGGACGACCACTTG) (SEQ. ID. NO. 3) and BNFD31-CR (GACTGGACCAACGAGGAATG) (SEQ. ID. NO. 4) and fad32 fragments amplified by the primer pairs BNFD32-CF (CAAGAATTTGTCCCACAGTACAC) (SEQ. ID. NO. 14) and BNFD32-CR (CAACTGTTGTTAATCCTCCACG) (SEQ. ID. NO. 15) were cloned because these fragments covered more sequences of each gene. Seven DMS100 clones and six Quantum clones of fad31 and six DMS100 clones and six Quantum clones of fad32 were sequenced. Sequence analysis and alignment revealed no sequence difference between DMS100 and Quantum for fad31 (data not shown). However, sequence alignment revealed a single nucleotide mutation, G to A, at the first base of 5' splice site of the third intron in fad32 gene (see FIG. 3). This intron corresponds to the intron 6 of the fad3 gene in *B. rapa* (Tanhuanpää, 2000) and *Arabidopsis* (Nishiuchi et al., 1994). The fad3 gene of *B. rapa* and *Arabidopsis* contains eight exons and seven introns, while the sequence examined covers exons 4 (partial), 5, 6 and 7 (partial) and introns 4, 5 and 6. This interpretation of exons/introns in the fad3 gene is supported by the fact that the fad3 gene sequence is highly conserved among sequenced *Brassica* species and *Arabidopsis*.

Plant introns contain highly conserved 5' splice sites (exon/intron junction—AG/GTAAG) and 3' splice sites (intron/exon junction—TGCAG/G. The first two nucleotides in the 5' splice site intron junction sequence, +1G and +2T, have shown 100% and 99% conservation, respectively, among over 1000 *Arabidopsis* introns studied (Lorkovic, 2000; and Brown, 1996). The accuracy of splicing depends on the mechanisms of intron signal recognition and the correct selection of 5' and 3' splice sites. Referring again to FIG. 3, the mutation of +1G to +1A at the 5' splice site (position 530) identified herein can abolish splicing or lead to exon skipping, i.e., the affected exon (exon 6) and both flanking introns are removed in a single splicing event (Lorkovic et al., 2000; Simpson et al., 1998). Such exon skipping could lead to synthesis of a polypeptide missing the amino acids encoded by exon 6 of the fad3 gene. The mutation could also block splicing at the normal 5' splice site and activate cryptic splice sites at different positions, which can cause cryptic splicing of the affected exon, together with the downstream intron (McCullough et al., 1993). Such cryptic splicing could lead early termination of translation and synthesis of a shorter polypeptide for delta-15 linoleate desaturase encoded by fad3. This will occur because the intron contains stop codons in all three possible reading frames and hence, exons 7 and 8 will remain untranslated. The incomplete translation of the fad3 can inactivate the enzyme and block the desaturation of linoleic acid (C18:2) to linolenic acid (C18:3), resulting in the decrease of C18:3 accumulation in canola seeds.

These data strongly suggest that the single nucleotide mutations identified in the fad2 and fad3 genes are factors that account for the increase in oleic acid and decrease in linolenic acid contents in the canola line DMS100. As shown in FIGS. 1 and 3, respectively, mutant-specific primers FAD2GM (CGCACCGTGATGGTTAACGGTTT) (SEQ. ID. NO. 5) and FAD3cGM (ATAAATAATGTTGATCTACTTAT) (SEQ. ID. NO. 6) were designed for purposes of detecting the mutant HOLL alleles of fad2 and fad32 using PCR amplification. Using the molecular markers of the present invention, these two mutations may serve to allow marker-assisted introgression into *Brassica* lines using the HOLL alleles of DMS100, its progeny or derivatives, or transgenic versions of its mutated fad2 and fad3 genes (SEQ. ID. NO. 7 (FIG. 1) and SEQ. ID. NO. 8 (FIG. 3), respectively) for purposes of developing HOLL canola.

Development of Mutant Allele-Specific SNP Markers for fad2 and fad3 Genes

Figure 8:
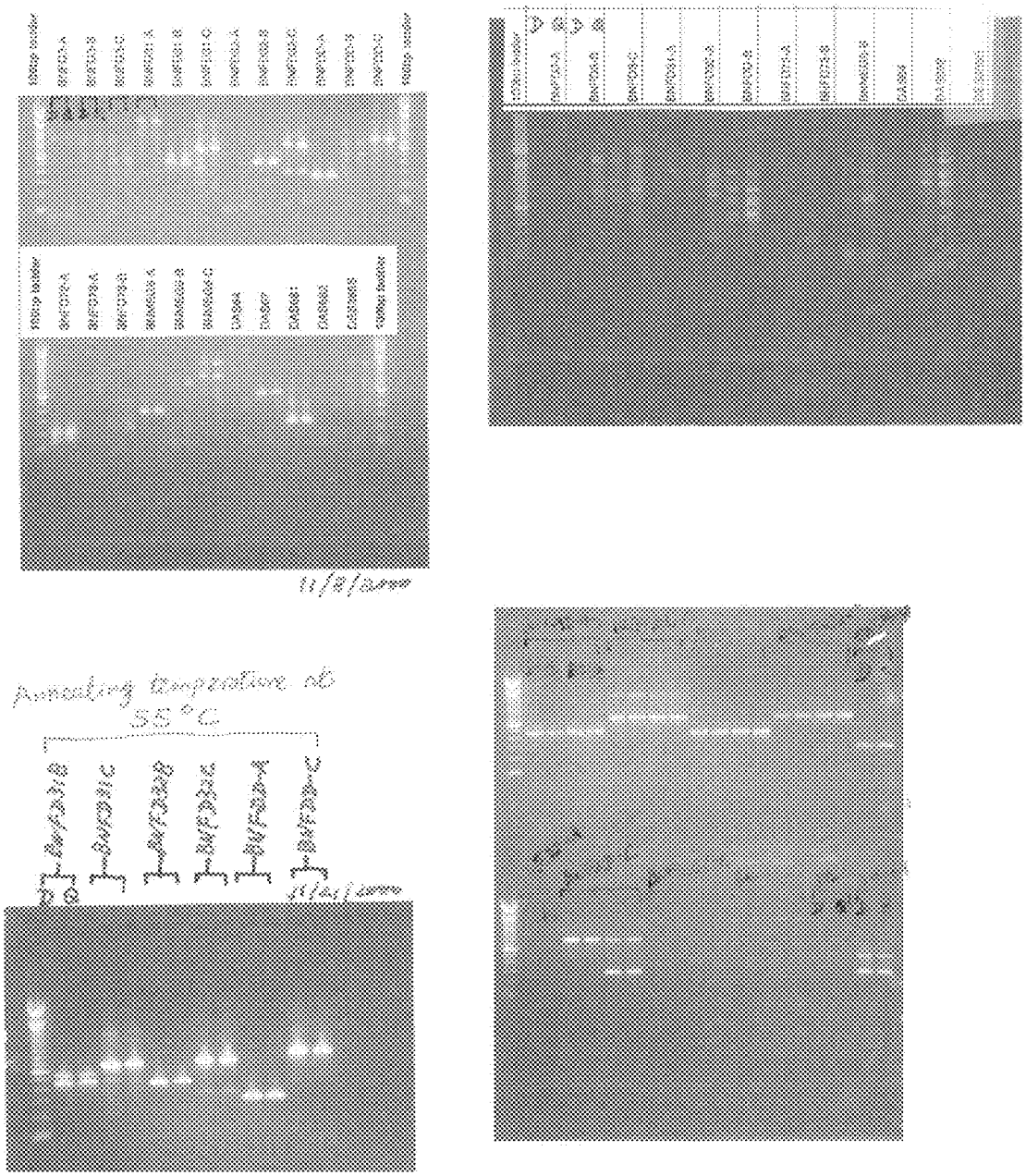

In a presently preferred embodiment, the single nucleotide mutations present in the fad2 and fad3 genes are used as SNP markers to tag the fad2 and fad3 genes for selection of high C18:1 and low C18:3 in canola breeding. Mutant-specific primers (FAD2GM: CGCACCGTGATGGTTAACGGTTT (SEQ. ID. NO. 5); and FAD3cGM: ATAAATAATGT-TGATCTACTTAT (SEQ. ID. NO. 6)) were designed in order to detect mutant alleles of fad2 and fad32 using PCR amplification. The primers were designed such that the mutated base (SNP) was at the 3' end of one of the primers for allele-specific PCR amplification (FIGS. 1 and 3). Lists of the various PCR markers developed and tested for HO/LL trait identification are provided in FIGS. 7 and 8. The primers specific to fad2 amplified a polymorphic band that was present in DMS100 and DNA bulks for high oleic acid (C18: 1), but were absent in Quantum and the DNA bulks for low oleic acid (FIG. 4).

This gene-specific marker was tested on a doubled haploid (DH) population derived from the cross of Quantum and DMS100, where it was found that the allele distribution was highly correlated to high C18:1 (see FIG. 4, Table 1). The fad3 allele-specific primers also amplified a polymorphic fragment that was present in DMS100 but absent in Quantum. The analysis with the DH population indicated that this allele-specific marker was statistically associated with low C18:3 (see FIG. 4, Table 1). Thus, two gene-specific PCR-based markers that directly tag fad2 and fad3 gene mutations were successfully developed. Given the disclosure, variations or derivatives of the markers disclosed herein (including markers of various types) based for example, on substantial homology over a sufficient number of base pairs, will be readily apparent to one of skill in the art.

Figure 5:
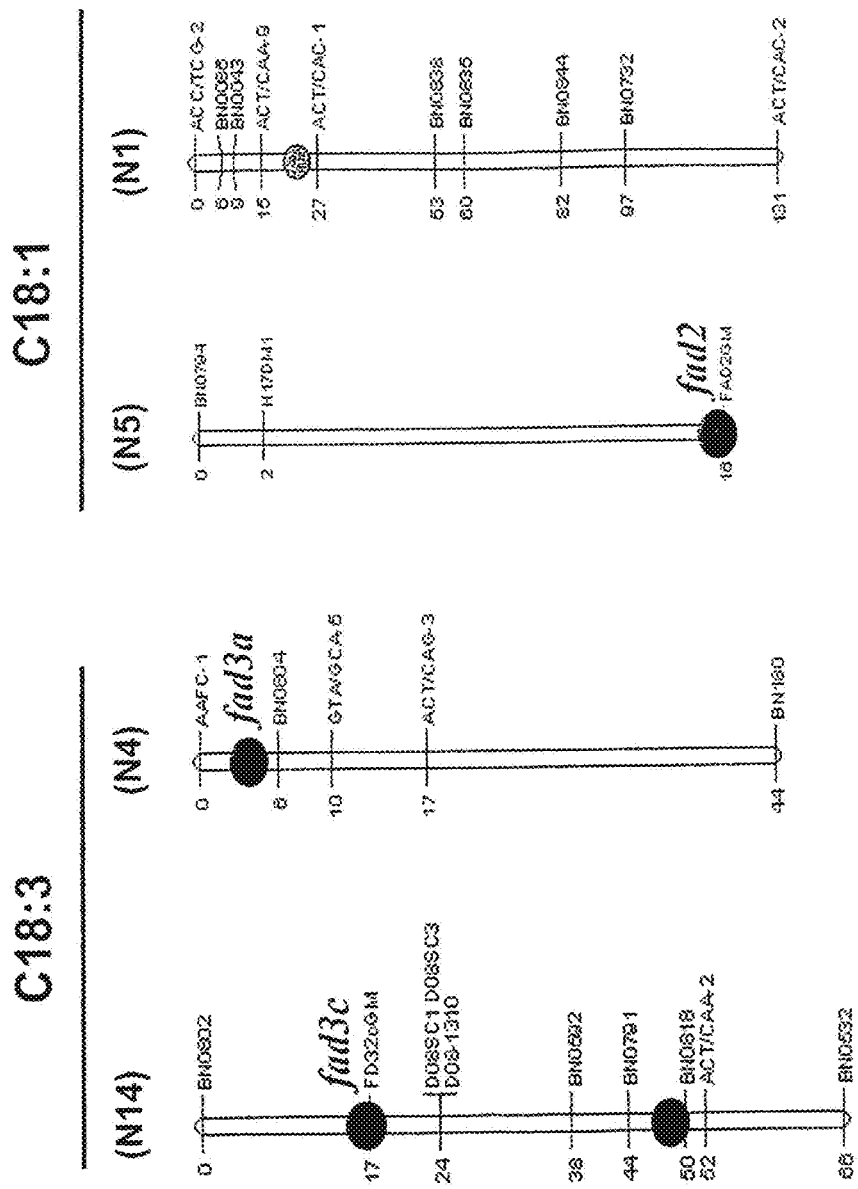
FIG. 5 is a QTL map of showing one major (N5) and one minor (N1) QTL region for high C18:1, and three QTL regions (N4 and N14) for low C18:3 detected by markers of the present invention.

Through genetic and QTL mapping using the DH population derived from the cross of Quantum×DMS100, one major (N5) and one minor (N1) QTL region for high C18:1, and three QTL regions (N4 and N14) for low C18:3 have been found (FIG. 5). This QTL mapping result is consistent with the genetic analysis that high C18:1 is controlled by one major gene and low C18:3 is controlled by multiple genes. The fad2 gene-based marker was located exactly at the mapped location of the major QTL locus for C18:1, supporting the fact that this QTL corresponds to the functional fad2 gene that is affected by the mutation in DMS100. This is also consistent with the previous studies that the fad2 gene is located on the linkage group N5 (Schierholt, 2000). The location of the fad3 gene-based marker matches exactly with the mapped location of one of the major QTL loci for C18:3 on the linkage group 14 (C genome), supporting the conclusion that this QTL is the fad3c (fad3 in the C genome, previously called fad32) gene and it is also affected by the second mutation in DMS100.

For molecular marker methods, see generally, The DNA Revolution by Andrew H. Paterson 1996 (Chapter 2) in: *Genome Mapping in Plants* (ed. Andrew H. Paterson) by Academic Press/R. G. Landis Company, Austin, Tex., pp. 7-21.

All publications, patents, and patent applications cited herein are hereby incorporated by reference. Unless otherwise noted herein, standard methods of DNA purification, restriction enzyme digestion, agarose gel analysis, DNA fragment isolation, ligation and transformation may be used for purposes of the present invention. Such methods are described in, for example, Sambrook et al., *Molecular Cloning: A Laboratory Manual*, Cold Spring Harbor Laboratory Press (2d ed., 1989), and Ausubel et al., *Current Protocols in Molecular Biology* (New York: John Wiley and Sons) (1987), both of which are also incorporated by reference herein.

The present invention has of necessity been discussed herein by reference to certain specific methods and materials. The enumeration of these methods and materials was merely illustrative, and in no way constitutes any limitation on the scope of the present invention. It is to be expected that those skilled in the art may discern and practice variations of or alternatives to the specific teachings provided herein, without departing from the scope of the present invention.

EXAMPLES

Example 1

Plant Material

Canola varieties DMS100 (mutant type) and Quantum (wild type) were used in this study for cloning of fad2 (fatty acid desaturase-2) and fad3 (fatty acid desaturase-3) alleles. DMS100 is a HOLL (High Oleic and Low Linolenic) line with oleic acid content at about 77% and linolenic acid content at about 3%. It is derived from an F4 bulk of a single F3 plant selection originating from the cross of Global×AG019 sister line. Quantum is a commercial variety and contains low oleic acid (~66%) and high linolenic acid (~7%) content. A double haploid (DH) population was developed by microspore culture from F1 plants of the cross between canola line Quantum and DMS100. The DH population comprised of 604 lines. A complete fatty acid analysis of the seeds of the DH lines and their parents was implemented by using gas chromatography. Of the 604 DH lines, 183 were randomly selected for marker analysis and mapping.

Example 2

Genomic DNA Extraction and Quantification

DNA of both parental lines and 183 DH lines was extracted from the leaves of two-week-old greenhouse-grown plants using Qiagen DNeasy 96 Plant Test Kit. The details of DNA extraction procedures are described in the DNeasy™ 96 Plant Test Kit Handbook. This kit allowed DNA to be extracted in a 96-well format for a high throughput extraction.

For DNA quantification, PicoGreen dye was diluted 200-fold into 1×TE buffer. In a microtiter plate, 100 µl of the diluted PicoGreen dye solution were added into each well and then 5 µl of each DNA sample or DNA standards (5 µg/ml, 10 µg/ml and 20 µg/ml) were added. The plate was then agitated on a plate shaker briefly and read using the Spectra Max GEMINIS XS microplate fluorometer from Molecular Devices.

Example 3

PCR Amplification

PCR amplification reactions contained 20 to 30 ng of genomic DNA, 0.25 µM 10-mer primer, 2.5 mM $MgCl_2$, 0.2 mM of each dNTP, 1×PCR buffer and 0.6 units of Taq DNA polymerase. Amplifications were performed in a GeneAmp PCR System 9700 programmed for 35 cycles of 45 seconds at 94° C., 30 seconds at 55° C. to 60° C., 1 minute at 72° C. and ending with 7 minutes at 72° C.

Example 4

Cloning of fad2 and fad3 Alleles

The fad2 fragments of parental lines DMS100 and wild-type line Quantum were amplified by using the primers homologous to *Arabidopsis* or *B. rapa* fad2 gene sequences (Tanhuanpää et al., 1998). The fad2 fragments amplified from each of the parents by the primers FAD2-2F and FAD2-6R were cloned and sequenced. The primers FAD2-2F and FAD2-6R correspond to the primers 2 and 6 of Tanhuanpää et al. (1998), respectively. The sequences of these two primers are:

```
FAD2-2F:    CAATCCCTCGCTCTTTCTCCTACC
FAD2-6R:    CCTTTCTTGTCACCTTCCCTGTCC
```

The DNA sequences of the fad31 and fad32 loci for C18:3 of *B. napus* were searched and retrieved from GenBank. The GenBank accession number for fad31 and fad32 are AF056569 and AF066570, respectively. Three pairs of primers for each fad31 and fad32 locus were designed from fad31 and fad32 gene sequences by using Primer Express primer designing software (PE Applied Biosystems, Foster City, Calif.). The fad31 fragments amplified by the primers BNFD31-CF and BNFD31-CR and the fad32 fragments amplified by the primers BNFD32-CF and BNFD32-CR from each of the parents were cloned and sequenced.

The PCR amplification products of interest were resolved by agarose-gel electrophoresis, and the bands of interest were excised from the gel. The excised bands were placed in a microfuge tube containing sterilized water and heated for five minutes in boiling water. The dissolved DNA was amplified by PCR with the corresponding primer pairs. The amplified products were ligated to PCR2.1-TOPO cloning vector using a TA-cloning kit (Invitrogen Corp., San Diego, (Calif.) per manufacturer's instructions. The ligated products were then transformed into competent cells and plated on LB-agar plates containing ampicillin or kanamycin, X-GAL and IPTG to enable white/blue selection. White colonies in the transformation plates were picked and identification of the cloned PCR products were verified by a digest with the restriction enzyme EcoR I, which revealed the vector DNA fragment and the insert fragment of the expected size. The positive clones containing the insert were sequenced by Sequetech Corporation (Mountain View, Calif.).

Example 5

Invader Assay

Figure 6A:
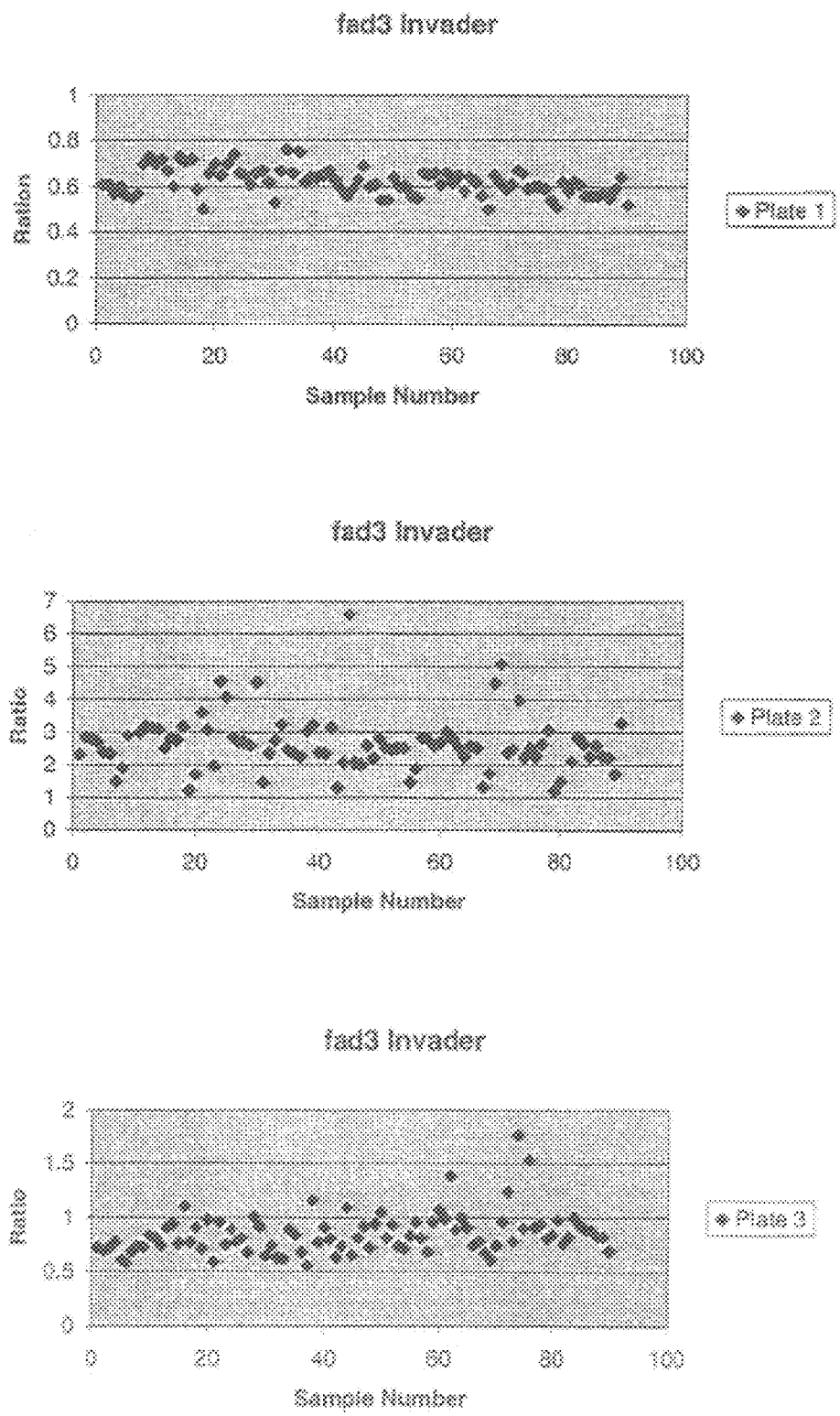
FIG. 6 provides Invader Assay results for mutant and wild-type alleles of fad2 and fad3 genes.
Figure 6B:
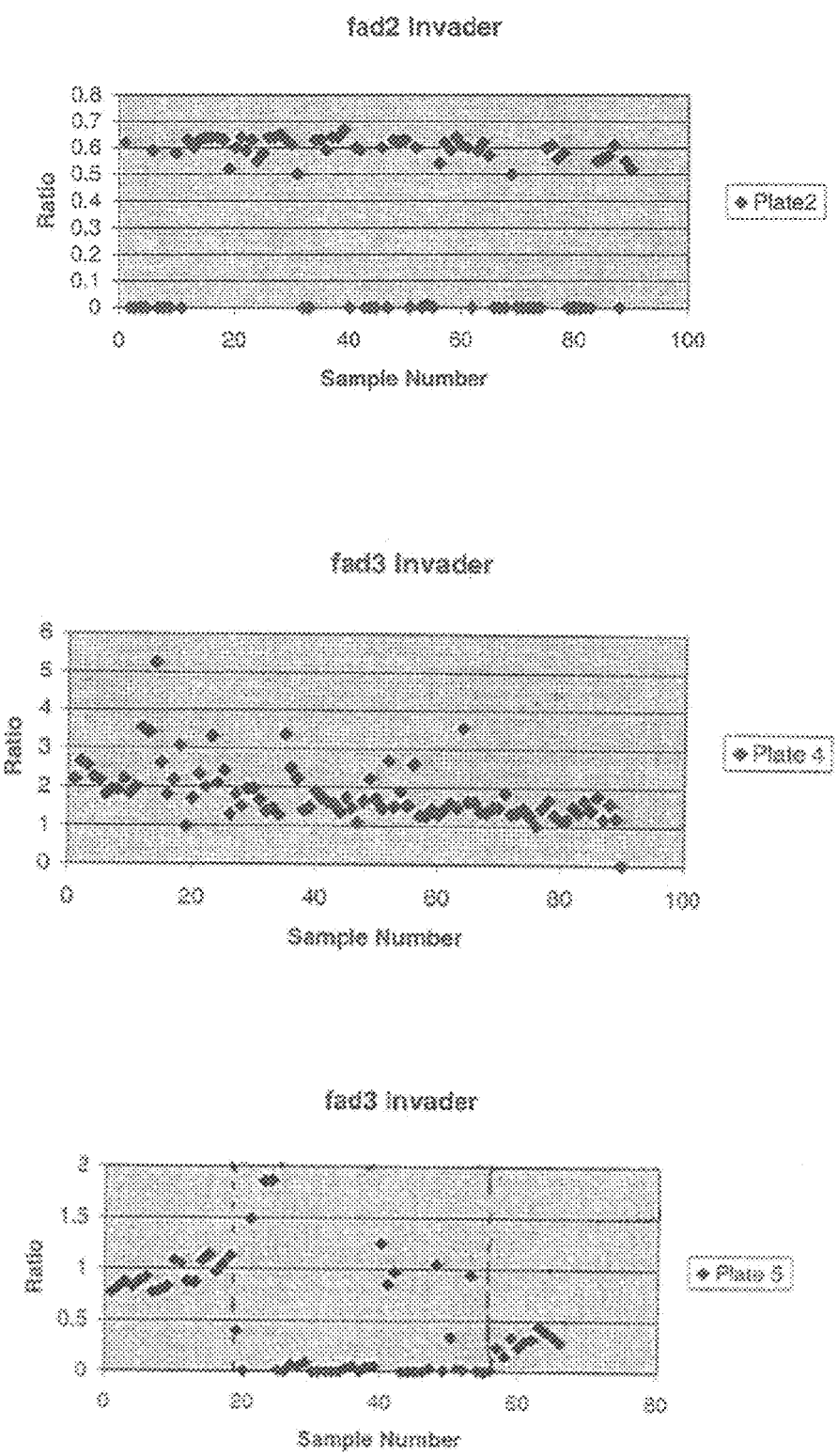
Figure 6D:
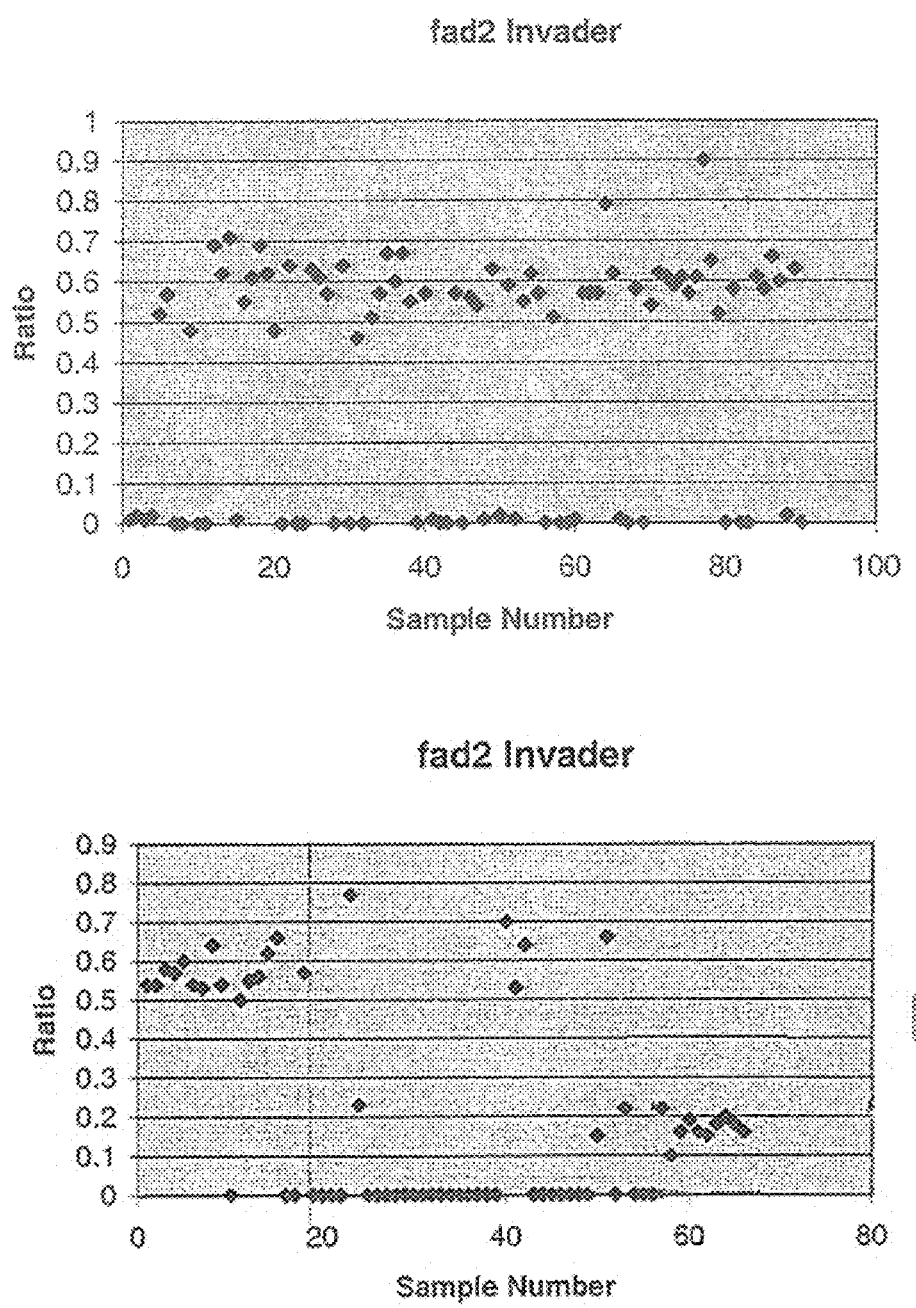

Invader Assay kits specific to fad2 and fad3 gene mutations were developed through Third Wave Technologies (Madison, Wis.). The concentration of DNA samples for Invader Assay was normalized to 15 ng/µl using QiaGen Bio-Robot 3000 (Valencia, Calif.). Invader Assay was performed in 96-well plates per manufacturer's instruction. In brief, DNA samples were denatured at 95° C. for ten minutes. Seven µl of the denatured DNA (15 ng/µl) and 8 µl of reaction mix (3 µl oligo mix and 5 µl of 24 mM $MgCl_2$) were added into each well of 96-well Invader Assay plates. Then, each reaction was overlaid with 15 µl of mineral oil and the plates were incubated in the BioOven III from St. John Associates, Inc. (Beltsville, Md.) at 63° C. for four hours. The reaction plates were read using the Spectra Max GEMINIS XS microplate fluorometer from Molecular Devices for fluorescent signals. Percent signal over background for the mutant allele was divided by the percent signal for wild-type allele for each sample to calculate the ratio. The genotypes of the samples were determined based on the calculated ratio. Results are provided in FIG. 6.

Example 6

Sequence and Data Analyses

The sequences were analyzed and aligned by using SeqWeb (version 2) web-based sequence analysis software in GCG software package (Wisconsin University). Linkage association between the markers and high oleic or low linolenic (HO/LL) traits were determined by t-test analysis. The genetic linkage map was generated with JoinMap V2.0 computer software using a minimum LOD of 3.0. Map distance was converted to centiMorgans using the Kosambi function. Putative QTL regions associated with the C18:1 and C18:3 were located by interval mapping using the MapQTL V 3.0 software. A LOD score of 3.0 was used to identify regions potentially affecting the two fatty acid traits.

REFERENCES

Arondel V., B. Lemieux, I. Hwang, S. Gibson, H. M. Goodman and C. R. Somerville (1992). Map-based cloning of a gene controlling Omega-3 fatty acid desaturation in *Arabidopsis*. *Science* 258:1353-1355.

Auld D. L., M. K. Heikkinen, D. A. Erickson, J. L. Sernyk, J. E. Romero (1992). Rapeseed mutants with reduced levels of polyunsaturated fatty acids and increased levels of oleic acid. *Crop Sci.* 32:657-662.

Barret P., R. Delourme, D. Brunet, C. Jourdren, R. Horvais and M. Renard (1999). Mutations in L1 and L2 genes of *Brassica napus* L. induce low linolenic acid content in the seeds. *GCIRC* 1999 Canberra, Australia.

Brown J. W. S. (1996). *Arabidopsis* intron mutations and pre-mRNA splicing. *Plant J.* 10:771-780.

Brunel D., N. Froger and G. Pelletier (1999). Development of amplified consensus genetic markers (ACGM) in *Brassica napus* from *Arabidopsis thaliana* sequences of known biological function. *Genome* 12:387-402.

Canvin D. T. (1965). The effect of temperature on the oil content and fatty acid composition of the oils from several oil seed crops. *Canadian Journal of Botany* 43:63-69.

Debonte L. A. and W. D. Hitz. Canola oil having increased oleic acid and decreased linolenic acid content and its manufacture using transgenic plants. CODEN: USXXAM. U. S. Pat. No. 5,850,026 A 981215. Application: US 96-675650 960703. CAN 130:65607.

Chen J. L. and W. D. Beversdorf (1990). A comparison of traditional and haploid-derived populations of oilseed rape (*Brassica napus* L.) for fatty acid composition of the seed oil. *Euphytica* 51:59-65.

Deng X. and R. Scarth (1998). Temperature effects on fatty acid composition during development of low linolenic oilseed rape (*Brassica napus* L.). *Journal of the American Oil Chemists' Society* 75:759-766.

J. L. Harwood (1999). *Lipid Synthesis and Manufacture* (ed. F. D. Gunstone), Sheffield Academic Press, Sheffield.

Hu J., C. Quiros, P. Arus, D. Struss and G. Röbbelen (1995). Mapping of a gene determining linolenic acid concentration in rapeseed with DNA-based markers. *Theor. Appl. Genet.* 90:258-262.

Hu J., G. Li, D. Struss and C. F. Quiros (1999). SCAR and RAPD markers associated with 18-carbon fatty acids in rapeseed, *Brassica napus*. *Plant Breeding* 118:145-150.

Jourdren C., P. Barret, D. Brunel, R. Delourme and M. Renard (1996). Specific molecular marker of the genes controlling linolenic acid content in rapeseed. *TAG* 93:512-518.

Kondra Z. P. and P. M. Thomas (1975). Inheritance of oleic, linoleic and linolenic acids in seed oil of rapeseed (*Brassica napus*). *Can. J. Plant Sci.* 55:205-210.

Lorkovic Z. J., D. A. W. Kirk, M. H. L. Lambermon and W. Filipowicz (2000). Pre-mRNA splicing in higher plants. *Trends in Plant Science* 5:160-167.

McCullough A. J., H. Lou and M. A. Schuler (1993). Factors affecting authentic 5' splice site selection in plant nuclei. *Mol. Cell. Biol.* 13:1323-1331.

Nishiuchi T., M. Nishimura, V. Arondel and K. Iba (1994). Genomic nucleotide sequence of a gene encoding a microsomal ω-3 fatty acid desaturase from *Arabidopsis thaliana*. *Plant Physiol.* 105:767-768.

Prakash S. and K. Hinata (1980). Taxonomy, cytogenetics, and origin of crop *Brassica*, a review. *Opera. Bot.* 55:1-59.

Rajcan I., K. J. Kasha, L. S. Kott and W. D. Beversdorf (1999). Detection of molecular markers associated with linolenic and erucic acid levels in spring rapeseed (*Brassica napus*). *Euphytica* 105:173-181.

Rakow G. (1973). Selection of linol- and linolenic acid in rapeseed after mutagenic treatment. *Plant J.* 69:205-209.

Rücker B. and G. Röbbelen (1996). Impact of low linolenic acid content on seed yield of winter oilseed rape (*Brassica napus* L.). *Plant Breeding* 115:226-230.

Scheffler J. A., A. G. Sharpe, H. Schmidt, P. Sperling, I. A. P. Parkin, W. Lühs, D. J. Lydiate and E. Heinz (1997). Desaturase multigene families of *Brassica napus* arose through genome duplication. *Theor. Appl. Genet.* 94:583-591.

Schierholt A., B. Rücker and H. C. Becker Ecke (2001). Inheritance of high oleic acid mutations in winter oilseed rape (*Brassica napus* L.). *Crop Sci.* 41:1444-1449.

Schierholt A., H. C. Becker and W. Ecke (2000). Mapping a high oleic acid mutation in winter oilseed rape (*Brassica napus* L.). *Theor. Appl. Genet.* 101:897-901.

Schierholt A. and H. C. Becker (1999). Genetic and environmental variability of high oleic acid content in winter oilseed rape. *GCIRC* 1999. Canberra, Australia.

Simpson C. G., C. McQuade, J. Lyon, and J. W. S. Brown (1998). Characterization of exon skipping mutants of the COP1 gene from *Arabidopsis*. *Plant J.* 17:125-131.

Somers D. J., K. R. D. Friesen and G. Rakow (1998). Identification of molecular markers associated with linoleic acid desaturation in *Brassica napus*. *Theor. Appl. Genet.* 96:897-903.

Song K. M., J. Y. Suzuki, M. K. Slocum, P. H. Williams, and T. C. Osborn (1991). A linkage map of *Brassica rapa* (syn. campestris) based on restriction fragment length polymorphism loci. *Theor. Appl. Genet.* 82:296-304.

Tanhuanpää P. (2000). Mapping and cloning of Fad3 gene in *Brassica rapa* subsp. *Oleifera*. GenBank direct submission. GenBank Accession AF308975, AF308976, AF308977 and AF308978.

Tanhuanpää P., J. Vilkki and M. Vihinen (1998). Mapping and cloning of FAD2 gene to develop allele-specific PCR for oleic acid in spring turnip rape (*Brassica rapa* ssp. *oleifera*). *Molecular Breeding* 4:543-550.

Tanhuanpää P. K., J. P. Vilkki and H. J. Vilkki (1995). Association of a RAPD marker with linolenic acid concentration in the seed oil of rapeseed (*Brassica napus* L.). *Genome* 38:414-416.

Thompson K. F. (1983). Breeding winter oilseed rape, *Brassica napus*. *Adv. Appl. Biol.* 7:1-104.

Thormann C. E., J. Romero, J. Mantet and T. C. Osborn (1996). Mapping loci controlling the concentrations of erucic and linolenic acids in seed oil of *Brassica napus* L. *Theor. App. Genet.* 93:282-286.

Wong R., J. D. Patel, I. Grant, J. Parker, D. Charne, M. Elhalwagy and E. Sys (1991). The development of high oleic canola. *GCIRC* 1991 Congress, Saskatoon, Canada. A16:53.

Yadav N. S., A. Wierzbicki, M. Aegerter, C. S. Caster, L. Perez-Grau, A. J. Kinney, W. D. Hitz, J. R. Booth Jr., B. Schweiger, K. L. Stecca, S. M. Allen, M. Blackwell, R. S. Reiter, T. J. Carlson, S. H. Russell, K. A. Feldmann, J. Pierce and J. Browse (1993). Cloning of higher plant ω-3 fatty acid desaturases. *Plant Physiol.* 103:467-476.

Yermanos D. M and J. R. Goodin (1965). Effects of temperatures during plant development on fatty acid composition of linseed oil. *Agronomy* 1 57:453-454.

SEQUENCE LISTING

```
<160> NUMBER OF SEQ ID NOS: 15

<210> SEQ ID NO 1
<211> LENGTH: 24
<212> TYPE: DNA
<213> ORGANISM: Brassica napus

<400> SEQUENCE: 1
caatccctcg ctctttctcc tacc                                    24

<210> SEQ ID NO 2
<211> LENGTH: 24
<212> TYPE: DNA
<213> ORGANISM: Brassica napus

<400> SEQUENCE: 2
cctttcttgt caccttccct gtcc                                    24

<210> SEQ ID NO 3
<211> LENGTH: 20
<212> TYPE: DNA
<213> ORGANISM: Brassica napus

<400> SEQUENCE: 3
gaggcttgga cgaccacttg                                         20
```

```
<210> SEQ ID NO 4
<211> LENGTH: 20
<212> TYPE: DNA
<213> ORGANISM: Brassica napus

<400> SEQUENCE: 4
gactggacca acgaggaatg                                                  20

<210> SEQ ID NO 5
<211> LENGTH: 23
<212> TYPE: DNA
<213> ORGANISM: Brassica napus

<400> SEQUENCE: 5
cgcaccgtga tggttaacgg ttt                                              23

<210> SEQ ID NO 6
<211> LENGTH: 23
<212> TYPE: DNA
<213> ORGANISM: Brassica napus

<400> SEQUENCE: 6
ataaataatg ttgatctact tat                                              23

<210> SEQ ID NO 7
<211> LENGTH: 985
<212> TYPE: DNA
<213> ORGANISM: Brassica napus

<400> SEQUENCE: 7
caatccctcg ctctttctcc tacctcatct gggacatcat catagcctcc tgcttctact      60
acgtcgccac cacttacttc cctctcctcc ctcaccctct ctcctacttc gcctggcctc     120
tctactgggc ctgccagggc tgcgtcctaa ccggcgtctg ggtcatagcc cacgagtgcg     180
gccaccacgc cttcagcgac taccagtggc tggacgacac cgtcggcctc atcttccact     240
ccttcctcct cgtcccttac ttctcctgga agtacagtca tcgacgccac cattccaaca     300
ctggctccct cgagagagac gaagtgtttg tccccaagaa gaagtcagac atcaagtggt     360
acggcaagta cctcaacaac cctttgggac gcaccgtgat gttaacggtt cagttcactc     420
tcggctggcc tttgtactta gccttcaacg tctcggggag accttacgac ggcggcttcg     480
cttgccattt ccaccccaac gctcccatct acaacgaccg tgagcgtctc cagatataca     540
tctccgacgc tggcatcctc gccgtctgct acggtctcta ccgctacgct gctgtccaag     600
gagttgcctc gatggtctgc ttctacggag ttcctcttct gattgtcaac gggttcttag     660
ttttgatcac ttacttgcag cacacgcatc cttccctgcc tcactatgac tcgtctgagt     720
gggattggtt gagggagct ttggccaccg ttgacagaga ctacggaatc ttgaacaagg     780
tcttccacaa tatcacggac acgcacgtgg cgcatcacct gttctcgacc atgccgcatt     840
atcatgcgat ggaagctacg aaggcgataa agccgatact gggagagtat tatcagttcg     900
atgggacgcc ggtggttaag gcgatgtgga gggaggcgaa ggagtgtatc tatgtggaac     960
cggacaggga aggtgacaag aaagg                                          985

<210> SEQ ID NO 8
<211> LENGTH: 985
<212> TYPE: DNA
<213> ORGANISM: Brassica napus

<400> SEQUENCE: 8
```

```
caatccctcg ctctttctcc tacctcatct gggacatcat catagcctcc tgcttctact    60
acgtcgccac cacttacttc cctctcctcc ctcaccctct ctcctacttc gcctggcctc   120
tctactgggc ctgccagggc tgcgtcctaa ccggcgtctg ggtcatagcc cacgagtgcg   180
gccaccacgc cttcagcgac taccagtggc tggacgacac cgtcggcctc atcttccact   240
ccttcctcct cgtcccttac ttctcctgga agtacagtca tcgacgccac cattccaaca   300
ctggctccct cgagagagac gaagtgtttg tccccaagaa gaagtcagac atcaagtggt   360
acggcaagta cctcaacaac cctttgggac gcaccgtgat gttaacggtt cagttcactc   420
tcggctggcc tttgtactta gccttcaacg tctcggggag accttacgac ggcggcttcg   480
cttgccattt ccaccccaac gctcccatct acaacgaccg tgagcgtctc cagatataca   540
tctccgacgc tggcatcctc gccgtctgct acggtctcta ccgctacgct gctgtccaag   600
gagttgcctc gatggtctgc ttctacggag ttcctcttct gattgtcaac gggttcttag   660
ttttgatcac ttacttgcag cacacgcatc cttccctgcc tcactatgac tcgtctgagt   720
gggattggtt gaggggagct ttggccaccg ttgacagaga ctacggaatc ttgaacaagg   780
tcttccacaa tatccggac acgcacgtgg cgcatcacct gttctcgacc atgccgcatt   840
atcatgcgat ggaagctacg aaggcgataa agccgatact gggagagtat tatcagttcg   900
atgggacgcc ggtggttaag gcgatgtgga gggaggcgaa ggagtgtatc tatgtggaac   960
cggacaggga aggtgacaag aaagg                                         985
```

<210> SEQ ID NO 9
<211> LENGTH: 324
<212> TYPE: PRT
<213> ORGANISM: Brassica napus

<400> SEQUENCE: 9

```
Arg Ser Phe Ser Tyr Leu Ile Trp Asp Ile Ile Ala Ser Cys Phe
1               5                   10                  15

Tyr Tyr Val Ala Thr Thr Tyr Phe Pro Leu Leu Pro His Pro Leu Ser
                20                  25                  30

Tyr Phe Ala Trp Pro Leu Tyr Trp Ala Cys Gln Gly Cys Val Leu Thr
            35                  40                  45

Gly Val Trp Val Ile Ala His Glu Cys Gly His His Ala Phe Ser Asp
        50                  55                  60

Tyr Gln Trp Leu Asp Asp Thr Val Gly Leu Ile Phe His Ser Phe Leu
65                  70                  75                  80

Leu Val Pro Tyr Phe Ser Trp Lys Tyr Ser His Arg Arg His Ser
                85                  90                  95

Asn Thr Gly Ser Leu Glu Arg Asp Glu Val Phe Val Pro Lys Lys Lys
                100                 105                 110

Ser Asp Ile Lys Trp Tyr Gly Lys Tyr Leu Asn Asn Pro Leu Gly Arg
            115                 120                 125

Thr Val Met Leu Thr Val Phe Thr Leu Gly Trp Pro Leu Tyr Leu Ala
        130                 135                 140

Phe Asn Val Ser Gly Arg Pro Tyr Asp Gly Gly Phe Ala Cys His Phe
145                 150                 155                 160

His Pro Asn Ala Pro Ile Tyr Asn Asp Arg Glu Arg Leu Gln Ile Tyr
                165                 170                 175

Ile Ser Asp Ala Gly Ile Leu Ala Val Cys Tyr Gly Leu Tyr Arg Tyr
            180                 185                 190
```

```
Ala Ala Val Gln Gly Val Ala Ser Met Val Cys Phe Tyr Gly Val Pro
            195                 200                 205

Leu Leu Ile Val Asn Gly Phe Leu Val Leu Ile Thr Tyr Leu Gln His
210                 215                 220

Thr His Pro Ser Leu Pro His Tyr Asp Ser Ser Glu Trp Asp Trp Leu
225                 230                 235                 240

Arg Gly Ala Leu Ala Thr Val Asp Arg Asp Tyr Gly Ile Leu Asn Lys
            245                 250                 255

Val Phe His Asn Ile Thr Asp Thr His Val Ala His His Leu Phe Ser
                260                 265                 270

Thr Met Pro His Tyr His Ala Met Glu Ala Thr Lys Ala Ile Lys Pro
            275                 280                 285

Ile Leu Gly Glu Tyr Tyr Gln Phe Asp Gly Thr Pro Val Val Lys Ala
290                 295                 300

Met Trp Arg Glu Ala Lys Glu Cys Ile Tyr Val Glu Pro Asp Arg Glu
305                 310                 315                 320

Gly Asp Lys Lys

<210> SEQ ID NO 10
<211> LENGTH: 275
<212> TYPE: PRT
<213> ORGANISM: Brassica napus

<400> SEQUENCE: 10

Arg Ser Phe Ser Tyr Leu Ile Trp Asp Ile Ile Ala Ser Cys Phe
1               5                   10                  15

Tyr Tyr Val Ala Thr Thr Tyr Phe Pro Leu Leu Pro His Pro Leu Ser
                20                  25                  30

Tyr Phe Ala Trp Pro Leu Tyr Trp Ala Cys Gln Gly Cys Val Leu Thr
            35                  40                  45

Gly Val Leu Glu Arg Asp Glu Val Phe Val Pro Lys Lys Lys Ser Asp
        50                  55                  60

Ile Lys Trp Tyr Gly Lys Tyr Leu Asn Asn Pro Leu Gly Arg Thr Val
65                  70                  75                  80

Met Leu Thr Val Gln Phe Thr Leu Gly Trp Pro Leu Tyr Leu Ala Phe
                85                  90                  95

Asn Val Ser Gly Arg Pro Tyr Asp Gly Gly Phe Ala Cys His Phe His
            100                 105                 110

Pro Asn Ala Pro Ile Tyr Asn Asp Arg Glu Arg Leu Gln Ile Tyr Ile
        115                 120                 125

Ser Asp Ala Gly Ile Leu Ala Val Cys Tyr Gly Leu Tyr Arg Tyr Ala
130                 135                 140

Ala Val Gln Gly Val Ala Ser Met Val Cys Phe Tyr Gly Val Pro Leu
145                 150                 155                 160

Leu Ile Val Asn Gly Phe Leu Val Leu Ile Thr Tyr Leu Gln His Thr
                165                 170                 175

His Pro Ser Leu Pro His Tyr Asp Ser Ser Glu Trp Asp Trp Leu Arg
            180                 185                 190

Gly Ala Leu Ala Thr Val Asp Arg Asp Tyr Gly Ile Leu Asn Lys Val
        195                 200                 205

Phe His Asn Ile Thr Asp Thr His Val Ala His His Leu Phe Ser Thr
210                 215                 220

Met Pro His Tyr His Ala Met Glu Ala Thr Lys Ala Ile Lys Pro Ile
225                 230                 235                 240
```

-continued

Leu Gly Glu Tyr Tyr Gln Phe Asp Gly Thr Pro Val Val Lys Ala Met
                245                 250                 255

Trp Arg Glu Ala Lys Glu Cys Ile Tyr Val Glu Pro Asp Arg Glu Gly
            260                 265                 270

Asp Lys Lys
        275

<210> SEQ ID NO 11
<211> LENGTH: 384
<212> TYPE: PRT
<213> ORGANISM: Brassica napus

<400> SEQUENCE: 11

Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
210                 215                 220

Gln Ile Tyr Ile Ser Asp Ala Gly Ile Leu Ala Val Cys Tyr Gly Leu
225                 230                 235                 240

Phe Arg Tyr Ala Ala Ala Gln Gly Val Ala Ser Met Val Cys Phe Tyr
                245                 250                 255

Gly Val Pro Leu Leu Ile Val Asn Gly Leu Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
            370                 375                 380

<210> SEQ ID NO 12
<211> LENGTH: 550
<212> TYPE: DNA
<213> ORGANISM: Brassica napus

<400> SEQUENCE: 12
caagaatttg tcccacagta cacggatgct cagatacact gtccctctcc ccatgctcgc    60
ttaccctctc tatctggtaa atcctaattc ctaattttc ttcctgatta taattacaat    120
tttgaatttt tagattttga gtattaacta aatataaatt aaatttgttt ggggatgact    180
acagtggtac agaagtcctg gtaaagaagg gtcacattat aacccataca gtagtttatt    240
tgccccaagc gagagaaagc ttattgcaac ttcaactact tgctggtcga tcgtgttggc    300
cactcttgtt tatctatcat tcctcgttgg tccagtcaca gttctaaaag tctatggtgt    360
tccttacatt gtaagtttca tatatttctt tattatatca ttgctaatat aatttgtttt    420
tgacataaaa gttttggaaa aatttcagat cttttgtaatg tggttggacg ctgtcacgta    480
cttgcatcat catggtcacg atgataagct gccttggtac agaggcaaga taagtagatc    540
aacattattt                                                            550

<210> SEQ ID NO 13
<211> LENGTH: 651
<212> TYPE: DNA
<213> ORGANISM: Brassica napus

<400> SEQUENCE: 13
caagaatttg tcccacagta cacggatgct cagatacact gtccctctcc ccatgctcgc    60
ttaccctctc tatctggtaa atcctaattc ctaattttc ttcctgatta taattacaat    120
tttgaatttt tagattttga gtattaacta aatataaatt aaatttgttt ggggatgact    180
acagtggtac agaagtcctg gtaaagaagg gtcacattat aacccataca gtagtttatt    240
tgccccaagc gagagaaagc ttattgcaac ttcaactact tgctggtcga tcgtgttggc    300
cactcttgtt tatctatcat tcctcgttgg tccagtcaca gttctaaaag tctatggtgt    360
tccttacatt gtaagtttca tatatttctt tattatatca ttgctaatat aatttgtttt    420
tgacataaaa gttttggaaa aatttcagat cttttgtaatg tggttggacg ctgtcacgta    480
cttgcatcat catggtcacg atgataagct gccttggtac agaggcaagg taagtagatc    540
aacattattt ataagaagca ataatgatta gtagttgaat aatctgaatt tttgatgttt    600
ttgtacaata ataggaatgg agttatttac gtggaggatt aacaacagtt g              651

<210> SEQ ID NO 14
<211> LENGTH: 23
<212> TYPE: DNA
<213> ORGANISM: Brassica napus

<400> SEQUENCE: 14
caagaatttg tcccacagta cac                                              23

```
<210> SEQ ID NO 15
<211> LENGTH: 22
<212> TYPE: DNA
<213> ORGANISM: Brassica napus

<400> SEQUENCE: 15
caactgttgt taatcctcca cg                                              22
```

What is claimed is:

1. A method for reliably and predictably introgressing traits for high oleic and/or low linolenic acid content into Brassica germplasm, said method comprising:
   identifying one or more nucleic acid markers that map to at least one of linkage groups N14, N4, N5 or N1, wherein the nucleic acid markers comprise a nucleotide sequence within a Fad2 gene that is capable of hybridizing to the nucleic acid molecule of SEQ ID NO:8 under high stringency conditions, but is not capable of hybridizing to the nucleic acid molecule of SEQ ID NO:7 under high stringency conditions;
   crossing a Brassica plant comprising the identified one or more nucleic acid markers with another Brassica plant that does not comprise the identified one or more markers; and
   selecting progeny from the cross that comprise the identified one or more nucleic acid markers.

2. The method of claim 1, wherein Brassica is canola.

3. A method for reliably and predictably introgressing traits for high oleic and/or low linolenic acid content into Brassica germplasm, said method comprising:
   identifying one or more nucleic acid markers that map to at least one of linkage groups N14, N4, N5 or N1, wherein the nucleic acid markers comprise a nucleotide sequence within a Fad3 gene that is capable of hybridizing to the nucleic acid molecule of SEQ ID NO:12 under high stringency conditions, but is not capable of hybridizing to the nucleic acid molecule of SEQ ID NO:13 under high stringency conditions;
   crossing a first Brassica plant comprising the identified one or more nucleic acid markers with a second Brassica plant that does not comprise the identified one or more markers; and
   selecting progeny from the cross that comprise the identified one or more nucleic acid markers.

4. The method of claim 3, wherein Brassica is canola.

5. A method for reliably and predictably introgressing traits for high oleic and/or low linolenic acid content into Brassica germplasm, said method comprising:
   identifying nucleic acid markers that map to at least one of linkage groups N14, N4, N5 or N1, wherein the nucleic acid markers comprise
      a nucleic acid marker comprising a nucleotide sequence within a Fad2 gene that is capable of hybridizing to the nucleic acid molecule of SEQ ID NO:8 under high stringency conditions, but is not capable of hybridizing to the nucleic acid molecule of SEQ ID NO:7 under high stringency conditions, and
      a nucleic acid marker comprising a nucleotide sequence within a Fad3 gene that is capable of hybridizing to the nucleic acid molecule of SEQ ID NO:12 under high stringency conditions, but is not capable of hybridizing to the nucleic acid molecule of SEQ ID NO:13 under high stringency conditions;
   crossing a Brassica plant comprising the identified markers with another Brassica plant that does not comprise the identified nucleic acid markers; and
   selecting progeny from the cross that comprise the identified nucleic acid markers.

6. The method of claim 5, wherein Brassica is canola.

7. A method for reliably and predictably introgressing traits for high oleic and/or low linolenic acid content into Brassica germplasm, said method comprising:
   identifying one or more nucleic acid markers that map to at least one of linkage groups N14, N4, N5 or N1, wherein the nucleic acid markers comprise SEQ ID NO:5;
   crossing a first Brassica plant comprising the identified one or more nucleic acid markers with a second Brassica plant; and
   selecting progeny from the cross that comprise the identified one or more nucleic acid markers.

8. The method according to claim 7, wherein Brassica is canola.

9. The method according to claim 7, wherein the one or more nucleic acid markers consist of a nucleic acid marker consisting of the polynucleotide of SEQ ID NO:5, wherein the presence of the nucleic acid marker consisting of the polynucleotide of SEQ ID NO:5 is determined in the first Brassica plant and the selected progeny by polymerase chain reaction, and wherein the Brassica plants are canola plants.

10. A method for reliably and predictably introgressing traits for high oleic and/or low linolenic acid content into Brassica germplasm, said method comprising:
    identifying one or more nucleic acid markers that map to at least one of linkage groups N14, N4, N5 or N1, wherein the nucleic acid markers comprise SEQ ID NO:6;
    crossing a first Brassica plant comprising the identified one or more nucleic acid markers with a second Brassica plant, wherein the first Brassica plant comprises a G to A mutation at the first base of the 5' splice site of the third intron in the Fad3 gene; and
    selecting progeny from the cross that comprise the identified one or more nucleic acid markers.

11. The method according to claim 10, wherein Brassica is canola.

12. The method according to claim 10, wherein the one or more nucleic acid markers consist of a nucleic acid marker consisting of the polynucleotide of SEQ ID NO:6, wherein the presence of the nucleic acid marker consisting of the polynucleotide of SEQ ID NO:6 is determined in the first Brassica plant and the selected progeny by polymerase chain reaction, and wherein the Brassica plants are canola plants.

13. A method for reliably and predictably introgressing traits for high oleic and/or low linolenic acid content into Brassica germplasm, said method comprising:
    identifying one or more nucleic acid markers that map to at least one of linkage groups N14, N4, N5 or N1, wherein the nucleic acid markers comprise
       a first nucleic acid marker comprising SEQ ID NO:5 and
       a second nucleic acid marker comprising SEQ ID NO:6;

crossing a first *Brassica* plant comprising the identified one or more nucleic acid markers with a second *Brassica* plant; and selecting progeny from the cross that comprise the identified one or more nucleic acid markers.

14. The method according to claim 13, wherein *Brassica* is canola.

15. The method according to claim 13, wherein the one or more nucleic acid markers consist of two nucleic acid markers, the first nucleic acid marker consisting of the polynucleotide of SEQ ID NO:5, and the second nucleic acid marker consisting of the polynucleotide of SEQ ID NO:6, wherein the presence of the two nucleic acid markers is determined in the first *Brassica* plant and the selected progeny by polymerase chain reaction, and wherein the *Brassica* plants are canola plants.

\* \* \* \* \*